US008032628B2

(12) United States Patent
Firminger et al.

(10) Patent No.: US 8,032,628 B2
(45) Date of Patent: Oct. 4, 2011

(54) SOLICITING DATA INDICATING AT LEAST ONE OBJECTIVE OCCURRENCE IN RESPONSE TO ACQUISITION OF DATA INDICATING AT LEAST ONE SUBJECTIVE USER STATE

(75) Inventors: Shawn P. Firminger, Redmond, WA (US); Jason Garms, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 300 days.

(21) Appl. No.: 12/378,288

(22) Filed: Feb. 11, 2009

(65) Prior Publication Data
US 2010/0131605 A1 May 27, 2010

Related U.S. Application Data

(63) Continuation-in-part of application No. 12/378,162, filed on Feb. 9, 2009, and a continuation-in-part of application No. 12/313,659, filed on Nov. 21, 2008, and a continuation-in-part of application No. 12/315,083, filed on Nov. 26, 2008, and a continuation-in-part of application No. 12/319,135, filed on Dec. 31, 2008, and a continuation-in-part of application No. 12/319,134, filed on Dec. 31, 2008.

(51) Int. Cl.
*G06F 15/16* (2006.01)

(52) U.S. Cl. ........ 709/224; 709/204; 709/206; 709/217; 705/2; 707/687; 707/755; 707/736; 706/11; 706/12; 706/52

(58) Field of Classification Search .................. 709/204, 709/206, 217; 705/2; 707/687, 755, 736; 706/11, 12, 52
See application file for complete search history.

(56) References Cited

U.S. PATENT DOCUMENTS 3,599,149 A 8/1971 Pardoe
(Continued)

FOREIGN PATENT DOCUMENTS

WO WO 99/18842 4/1999

OTHER PUBLICATIONS

Agger, Michael; "Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.

(Continued)

Primary Examiner — Jude Jean Gilles

(57) ABSTRACT

A computationally implemented method includes, but is not limited to: acquiring subjective user state data including data indicating at least one subjective user state associated with a user; soliciting, in response to the acquisition of the subjective user state data, objective occurrence data including data indicating occurrence of at least one objective occurrence; acquiring the objective occurrence data; and correlating the subjective user state data with the objective occurrence data. In addition to the foregoing, other method aspects are described in the claims, drawings, and text forming a part of the present disclosure.

43 Claims, 20 Drawing Sheets

U.S. PATENT DOCUMENTS

| | | | |
|---|---|---|---|
| 7,203,430 B2 * | 4/2007 | Ohta | 399/8 |
| 7,400,928 B2 | 7/2008 | Hatlestsad | |
| 7,627,544 B2 | 12/2009 | Chkodrov et al. | |
| 2003/0166277 A1 | 9/2003 | Zauderer et al. | |
| 2004/0103108 A1 | 5/2004 | Andreev et al. | |
| 2005/0102578 A1 | 5/2005 | Bliss et al. | |
| 2006/0034430 A1 | 2/2006 | Liakis | |
| 2007/0293731 A1 | 12/2007 | Downs et al. | |
| 2008/0034056 A1 | 2/2008 | Renger et al. | |
| 2008/0091515 A1 | 4/2008 | Thieberger et al. | |
| 2008/0215607 A1 | 9/2008 | Kaushansky et al. | |
| 2008/0218472 A1 | 9/2008 | Breen et al. | |
| 2009/0049154 A1 | 2/2009 | Ge | |
| 2009/0077658 A1 | 3/2009 | King et al. | |
| 2009/0132197 A1 | 5/2009 | Rubin et al. | |
| 2009/0240647 A1 | 9/2009 | Green et al. | |
| 2009/0276221 A1 | 11/2009 | Heiman et al. | |
| 2009/0326981 A1 | 12/2009 | Karkanias et al. | |
| 2010/0010866 A1 | 1/2010 | Bal et al. | |
| 2010/0088104 A1 | 4/2010 | DeRemer et al. | |

OTHER PUBLICATIONS

"Self-tracking links to get you started"; The Quantified Self: self knowledge through numbers; printed on Dec. 10, 2010; pp. 1-5; located at: http://quantifiedself.com/self-tracking-links-to-get-you-started/.

U.S. Appl. No. 12/462,201, Firminger et al.
U.S. Appl. No. 12/462,128, Firminger et al.
U.S. Appl. No. 12/459,854, Firminger et al.
U.S. Appl. No. 12/459,775, Firminger et al.
U.S. Appl. No. 12/456,433, Firminger et al.
U.S. Appl. No. 12/456,249, Firminger et al.
U.S. Appl. No. 12/455,317, Firminger et al.
U.S. Appl. No. 12/455,309, Firminger et al.
U.S. Appl. No. 12/387,487, Firminger et al.
U.S. Appl. No. 12/387,465, Firminger et al.
U.S. Appl. No. 12/384,779, Firminger et al.
U.S. Appl. No. 12/384,660, Firminger et al.
U.S. Appl. No. 12/383,817, Firminger et al.
U.S. Appl. No. 12/383,581, Firminger et al.
U.S. Appl. No. 12/380,573, Firminger et al.
U.S. Appl. No. 12/380,409, Firminger et al.
U.S. Appl. No. 12/378,162, Firminger et al.
U.S. Appl. No. 12/319,135, Firminger et al.
U.S. Appl. No. 12/319,134, Firminger et al.
U.S. Appl. No. 12/315,083, Firminger et al.
U.S. Appl. No. 12/313,659, Firminger et al.

Buchanan, Matt; "Twitter Toilet Tweets Your Poo"; gizmodo.com; bearing a date of May 18, 2009; pp. 1-2; located at http://gizmodo.com/5259381/twitter-toilet-tweets-your-poo; printed on Jul. 1, 2009.

Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the...; printed on Nov. 25, 2009.

Fox, Stuart; "The John, 2.0"; Popular Science; bearing a date of May 18, 2009; pp. 1-2; located at http://www.popsci.com/scitech/article/2009-05/john-20; printed on Jul. 1, 2009.

Frucci, Adam; "SNIF Dog Tags Track What Your Dog Does All Day; Spoiler: Eat, Sleep, Poop"; gizmodo.com; bearing a date of Jun. 10, 2009; pp. 1-2; located at http://i.gizmodo.com/5286076/snif-dog-tags-track-what-your-dog-does-all-day-spoiler-eat-sl...; printed on Jul. 1, 2009.

Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919...; printed on Nov. 25, 2009.

"hacklab.Toilet—a twitter-enabled toilet at hacklab.to"; aculei.net; bearing a date of May 18, 2009; pp. 1-8; located at http://aculei.net/~shardy/hacklabtoilet/; printed on Jul. 1, 2009.

June, Laura; "Apple patent filing shows off activity monitor for skiers, bikers"; engadget.com; bearing a date of Jun. 11, 2009; pp. 1-8; located at http://www.engadget.com/2009/06/11/apple-patent-filing-shows-off-a...; printed on Jul. 1, 2009.

Kraft, Caleb; "Twittering toilet"; Hack A Day; bearing a date of May 5, 2009; pp. 1-11; located at http://hackaday.com/2009/05/05/twittering-toilet/;printed on Jul. 1, 2009.

"Mobile pollution sensors deployed"; BBC news;bearing a date of Jun. 30, 2009; pp. 1-2; located at http://news.bbc.co.uk/2/hi/science/nature/8126498.stm; printed on Jul. 1, 2009; © BBC MMIX.

Morales, C. Romero et al.; "Using sequential pattern mining for links recommendation in adaptive hypermedia educational systems"; Current Developments in Technology-Assisted Education; bearing a date of 2006; pp. 1016-1020; © FORMATEX 2006.

Nesbit, J.C. et al.; "Sequential pattern analysis software for educational event data"; pp. 1-5.

Oliver, Sam; "Apple developing activity monitor for skiers, snowboarders, bikers"; AppleInsider; bearing a date of Jun. 11, 2009; pp. 1-6; located at http://www.appleinsider.com/articles/09/06/11/apple_developing_act...; printed on Jul. 1, 2009; AppleInsider © 1997-2008.

Rettner, Rachael; "Cell Phones Allow Everyone to Be a Scientist"; LiveScience; bearing a date of Jun. 4, 2009; pp. 1-3; located at http://www.livescience.com/technology/090604-mobile-sensor.html; printed on Jul. 1, 2009 © Imaginova Corp.

SPSS; "Find patterns in data that identify combinations of events that occur together"; SPSS Association Rule Components; bearing a date of 2002; pp. 1-5 © 2002 SPSS Inc.

SPSS; "Find sequential patterns in data to predict events more accurately"; SPSS Sequence Association™ Component; bearing a date of 2002; pp. 1-5; © 2002 SPSS Inc.

Hansen, et al.; "Microblogging—Facilitating Tacit Knowledge?"—A Second Year Term Paper; Information Management Study at Copenhagen Business School; 2008; pp. 1-42; located at http://www.scribd.com/doc/3460679/Microblogging-as-a-Facilitator-for-Tacit-Knowledge.

Reiss, M.; "Correlations Between Changes in Mental States and Thyroid Activity After Different Forms of Treatment"; The British Journal of Psychology—Journal of Mental Science; bearing dates of Mar. 6, 1954 and 1954; pp. 687-703 [Abstract only provided]; located at http://bjp.rcpsych.org/cgi/content/abstract/100/420/687; The Royal College of Psychiatrists.

* cited by examiner

102 Subjective User State Data Acquisition Module

202 Subjective User State Data Reception Module

204 User Interface Data Reception Module

206 Network Interface Data Reception Module

208 Time Data Acquisition Module

210 Time Stamp Acquisition Module

212 Time Interval Acquisition Module

214 Temporal Relationship Acquisition Module

FIG. 2a

103 Objective Occurrence Data Solicitation Module

215 Network Interface Solicitation Module

216 User Interface Solicitation Module

217 Requesting Module

218 Configuration Module

219 Directing/instructing Module

FIG. 2b

SOLICITING DATA INDICATING AT LEAST ONE OBJECTIVE OCCURRENCE IN RESPONSE TO ACQUISITION OF DATA INDICATING AT LEAST ONE SUBJECTIVE USER STATE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/378,162, entitled SOLICITING DATA INDICATING AT LEAST ONE OBJECTIVE OCCURRENCE IN RESPONSE TO ACQUISITION OF DATA INDICATING AT LEAST ONE SUBJECTIVE USER STATE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 9 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/313,659, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 21 Nov. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/315,083, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 26 Nov. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,135, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,134, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

A computationally implemented method includes, but is not limited to: acquiring subjective user state data including data indicating at least one subjective user state associated with a user; soliciting, in response to the acquisition of the subjective user state data, objective occurrence data including data indicating occurrence of at least one objective occurrence; acquiring the objective occurrence data; and correlating the subjective user state data with the objective occurrence data. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for acquiring subjective user state data including data indicating at least one subjective user state associated with a user; means for soliciting, in response to the acquisition of the subjective user state data, objective occurrence data including data indicating occurrence of at least one objective occurrence; means for acquiring the objective occurrence data; and means for correlating the subjective user state data with the objective occurrence data. In addition to the foregoing, other system aspects are described in the claims, drawings, and text forming a part of the present disclosure.

A computationally implemented system includes, but is not limited to: circuitry for acquiring subjective user state data including data indicating at least one subjective user state associated with a user; circuitry for soliciting, in response to the acquisition of the subjective user state data, objective occurrence data including data indicating occurrence of at least one objective occurrence; circuitry for acquiring the objective occurrence data; and circuitry for correlating the subjective user state data with the objective occurrence data. In addition to the foregoing, other system aspects are described in the claims, drawings, and text forming a part of the present disclosure.

A computer program product including a signal-bearing medium bearing one or more instructions for acquiring subjective user state data including data indicating at least one subjective user state associated with a user; one or more instructions for soliciting, in response to the acquisition of the subjective user state data, objective occurrence data including data indicating occurrence of at least one objective occurrence; one or more instructions for acquiring the objective occurrence data; and one or more instructions for correlating the subjective user state data with the objective occurrence data. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2a shows another perspective of the subjective user state data acquisition module 102 of the computing device 10 of FIG. 1b.

FIG. 2b shows another perspective of the objective occurrence data solicitation module 103 of the computing device 10 of FIG. 1b.

DETAILED DESCRIPTION

Figure 1A:
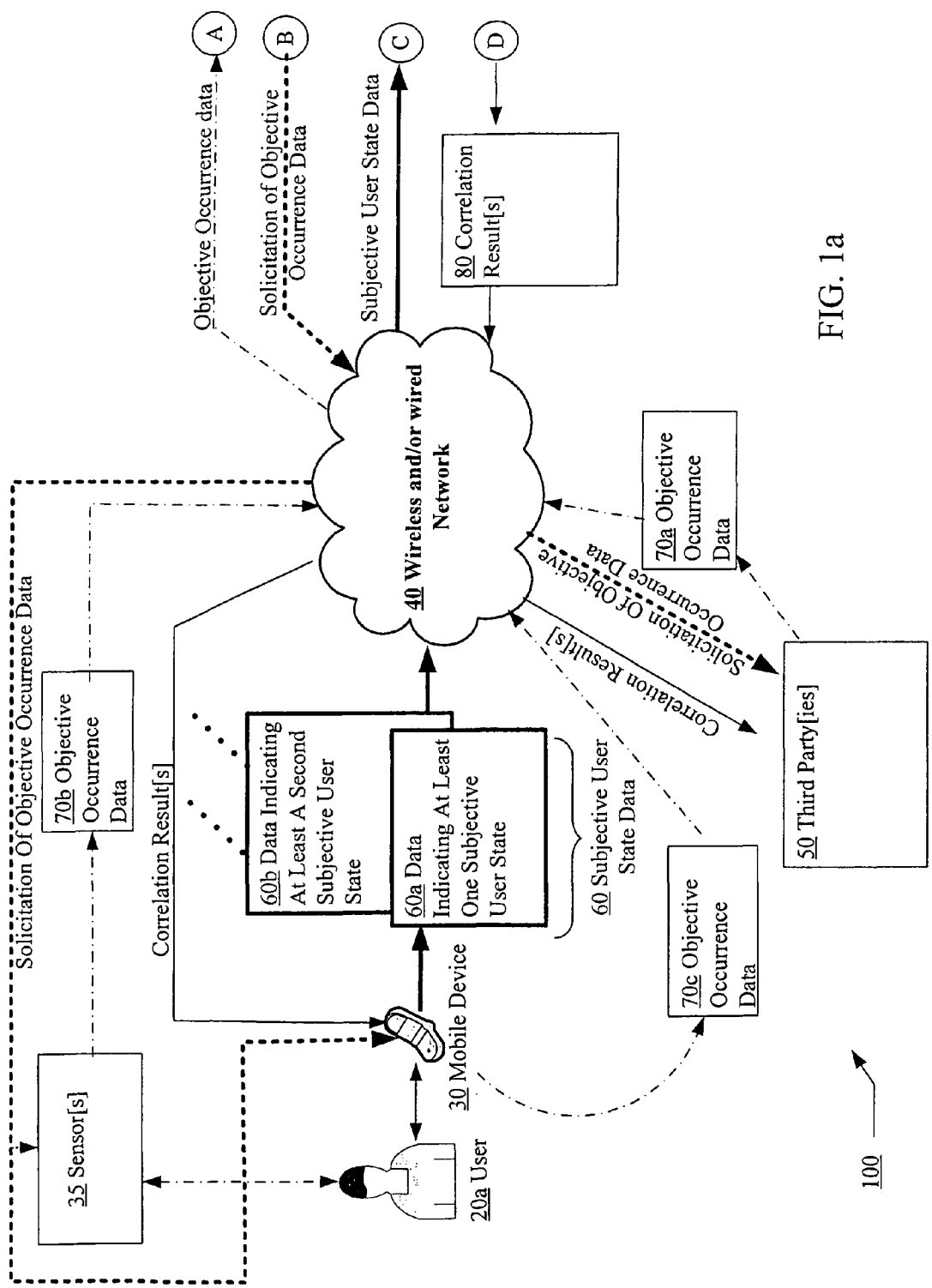
FIGS. 1a and 1b show a high-level block diagram of a computing device 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that is becoming increasingly popular in the computing/communication field is to electronically record one's feelings, thoughts, and other aspects of the person's everyday life onto an open diary. One place where such open diaries are maintained are at social networking sites commonly known as "blogs" where one or more users may report or post their thoughts and opinions on various topics, the latest news, and various other aspects of the users' everyday life. The process of reporting or posting blog entries is commonly referred to as blogging. Other social networking sites may allow users to update their personal information via, for example, social network status reports in which a user may report or post for others to view the latest status or other aspects of the user.

A more recent development in social networking is the introduction and explosive growth of microblogs in which individuals or users (referred to as "microbloggers") maintain open diaries at microblog websites (e.g., otherwise known as "twitters") by continuously or semi-continuously posting microblog entries. A microblog entry (e.g., "tweet") is typically a short text message that is usually not more than 140 characters long. The microblog entries posted by a microblogger may report on any aspect of the microblogger's daily life.

The various things that are typically posted through microblog entries may be categorized into one of at least two possible categories. The first category of things that may be reported through microblog entries are "objective occurrences" associated with the microblogger. Objective occurrences that are associated with a microblogger may be any characteristic, event, happening, or any other aspects associated with or are of interest to the microblogger that can be objectively reported by the microblogger, a third party, or by a device. These things would include, for example, food, medicine, or nutraceutical intake of the microblogger, certain physical characteristics of the microblogger such as blood sugar level or blood pressure that can be objectively measured, daily activities of the microblogger observable by others or by a device, external events that may not be directly related to the user such as the local weather or the performance of the stock market (which the microblogger may have an interest in), activities of others (e.g., spouse or boss) that may directly or indirectly affect the microblogger, and so forth.

A second category of things that may be reported or posted through microblogging entries include "subjective user states" of the microblogger. Subjective user states of a microblogger include any subjective state or status associated with the microblogger that can only be typically reported by the microblogger (e.g., generally cannot be reported by a third party or by a device). Such states including, for example, the subjective mental state of the microblogger (e.g., "I am feeling happy"), the subjective physical states of the microblogger (e.g., "my ankle is sore" or "my ankle does not hurt anymore" or "my vision is blurry"), and the subjective overall state of the microblogger (e.g., "I'm good" or "I'm well"). Note that the term "subjective overall state" as will be used herein refers to those subjective states that may not fit neatly into the other two categories of subjective user states described above (e.g., subjective mental states and subjective physical states). Although microblogs are being used to provide a wealth of personal information, they have thus far been primarily limited to their use as a means for providing commentaries and for maintaining open diaries.

In accordance with various embodiments, methods, systems, and computer program products are provided for, among other things, acquiring subjective user state data including data indicative of at least one subjective user state associated with a user and soliciting, in response to the acquisition of the subjective user state data, objective occurrence data including data indicating at least one objective occurrence. As will be further described herein, in some embodiments, the solicitation of the objective occurrence data may, in addition to be prompted by the acquisition of the subjective user state data, may be prompted by referencing historical data. Such historical data may be historical data that is associated with the user, associated with a group of users, associated with a segment of the general population, or associated with the general population.

The methods, systems, and computer program products may then correlate the subjective user state data (e.g., data that indicate one or more subjective user states of a user) with the objective occurrence data (e.g., data that indicate one or more objective occurrences associated with the user). By correlating the subjective user state data with the objective occurrence data, a causal relationship between one or more objective occurrences (e.g., cause) and one or more subjective user states (e.g., result) associated with a user (e.g., a blogger or microblogger) may be determined in various alternative embodiments. For example, determining that the last time a user ate a banana (e.g., objective occurrence), the user felt "good" (e.g., subjective user state) or determining whenever a user eats a banana the user always or sometimes feels good. Note that an objective occurrence does not need to occur prior to a corresponding subjective user state but instead, may occur subsequent or concurrently with the incidence of the subjective user state. For example, a person may become "gloomy" (e.g., subjective user state) whenever it is about to rain (e.g., objective occurrence) or a person may become gloomy while (e.g., concurrently) it is raining.

As briefly described above, a "subjective user state" is in reference to any state or status associated with a user (e.g., a blogger or microblogger) at any moment or interval in time that only the user can typically indicate or describe. Such states include, for example, the subjective mental state of the user (e.g., user is feeling sad), the subjective physical state (e.g., physical characteristic) of the user that only the user can typically indicate (e.g., a backache or an easing of a backache as opposed to blood pressure which can be reported by a blood pressure device and/or a third party), and the subjective overall state of the user (e.g., user is "good"). Examples of subjective mental states include, for example, happiness, sadness, depression, anger, frustration, elation, fear, alertness, sleepiness, and so forth. Examples of subjective physical states include, for example, the presence, easing, or absence of pain, blurry vision, hearing loss, upset stomach, physical exhaustion, and so forth. Subjective overall states may include any subjective user states that cannot be easily categorized as a subjective mental state or as a subjective physical state. Examples of overall states of a user that may be subjective user states include, for example, the user being good, bad, exhausted, lack of rest, wellness, and so forth.

In contrast, "objective occurrence data," which may also be referred to as "objective context data," may include data that indicate one or more objective occurrences associated with the user that occurred at particular intervals or points in time. An objective occurrence may be any physical characteristic, event, happenings, or any other aspect that may be associated with or is of interest to a user that can be objectively reported by at least a third party or a sensor device. Note, however, that such objective occurrence data does not have to be actually provided by a sensor device or by a third party, but instead, may be reported by the user himself or herself (e.g., via microblog entries). Examples of objectively reported occurrences that could be indicated by the objective occurrence data include, for example, a user's food, medicine, or nutraceutical intake, the user's location at any given point in time, a user's exercise routine, a user's physiological characteristics such as blood pressure, social or professional activities, the weather at a user's location, activities associated with third parties, occurrence of external events such as the performance of the stock market, and so forth.

The term "correlating" as will be used herein is in reference to a determination of one or more relationships between at least two variables. Alternatively, the term "correlating" may merely be in reference to the linking or associating of at least two variables. In the following exemplary embodiments, the first variable is subjective user state data that represents at least one subjective user state of a user and the second variable is objective occurrence data that represents at least one objective occurrence. In embodiments where the subjective user state data includes data that indicates multiple subjective user states, each of the subjective user states represented by the subjective user state data may be the same or similar type of subjective user state (e.g., user being happy) at different intervals or points in time. Alternatively, different types of subjective user state (e.g., user being happy and user being sad) may be represented by the subjective user state data. Similarly, in embodiments where multiple objective occurrences are indicated by the objective occurrence data, each of the objective occurrences may represent the same or similar type of objective occurrence (e.g., user exercising) at different intervals or points in time, or alternatively, different types of objective occurrence (e.g., user exercising and user resting).

Various techniques may be employed for correlating subjective user state data with objective occurrence data in various alternative embodiments. For example, in some embodiments, correlating the objective occurrence data with the subjective user state data may be accomplished by determining a sequential pattern associated with at least one subjective user state indicated by the subjective user state data and at least one objective occurrence indicated by the objective occurrence data. In other embodiments, correlating of the objective occurrence data with the subjective user state data may involve determining multiple sequential patterns associated with multiple subjective user states and multiple objective occurrences.

A sequential pattern, as will be described herein, may define time and/or temporal relationships between two or more events (e.g., one or more subjective user states and one or more objective occurrences). In order to determine a sequential pattern, objective occurrence data including data indicating at least one objective occurrence may be solicited (e.g., from a user, from one or more third party sources, or from one or more sensor devices) in response to an acquisition of subjective user state data including data indicating at least one subjective user state.

For example, if a user reports that the user felt gloomy on a particular day (e.g., subjective user state) then a solicitation (e.g., from the user or from a third party source such as a content provider) may be made about the local weather (e.g., objective occurrence). Such solicitation of objective occurrence data may be prompted based, at least in part, on the reporting of the subjective user state and based on historical data such as historical data that indicates or suggests that the user tends to get gloomy when the weather is bad (e.g., cloudy) or based on historical data that indicates that people in the general population tend to get gloomy whenever the weather is bad. In some embodiments, such historical data may indicate or define one or more historical sequential patterns of the user or of the general population as they relate to subjective user states and objective occurrences.

As briefly described above, a sequential pattern may merely indicate or represent the temporal relationship or relationships between at least one subjective user state and at least one objective occurrence (e.g., whether the incidence or occurrence of the at least one subjective user state occurred before, after, or at least partially concurrently with the incidence of the at least one objective occurrence). In alternative implementations, and as will be further described herein, a sequential pattern may indicate a more specific time relationship between the incidences of one or more subjective user states and the incidences of one or more objective occurrences. For example, a sequential pattern may represent the specific pattern of events (e.g., one or more objective occurrences and one or more subjective user states) that occurs along a timeline.

The following illustrative example is provided to describe how a sequential pattern associated with at least one subjective user state and at least one objective occurrence may be determined based, at least in part, on the temporal relationship between the incidence of the at least one subjective user state and the incidence of the at least one objective occurrence in accordance with some embodiments. For these embodiments, the determination of a sequential pattern may initially involve determining whether the incidence of the at least one subjective user state occurred within some predefined time increments of the incidence of the one objective occurrence. That is, it may be possible to infer that those subjective user states that did not occur within a certain time period from the incidence of an objective occurrence are not related or are unlikely related to the incidence of that objective occurrence.

For example, suppose a user during the course of a day eats a banana and also has a stomach ache sometime during the course of the day. If the consumption of the banana occurred in the early morning hours but the stomach ache did not occur until late that night, then the stomach ache may be unrelated to the consumption of the banana and may be disregarded. On the other hand, if the stomach ache had occurred within some predefined time increment, such as within 2 hours of consumption of the banana, then it may be concluded that there is a correlation or link between the stomach ache and the consumption of the banana. If so, a temporal relationship between the consumption of the banana and the occurrence of the stomach ache may be determined. Such a temporal relationship may be represented by a sequential pattern. Such a sequential pattern may simply indicate that the stomach ache (e.g., a subjective user state) occurred after (rather than before or concurrently) the consumption of banana (e.g., an objective occurrence).

As will be further described herein, other factors may also be referenced and examined in order to determine a sequential pattern and whether there is a relationship (e.g., causal relationship) between an objective occurrence and a subjective user state. These factors may include, for example, historical data (e.g., historical medical data such as genetic data or past history of the user or historical data related to the general population regarding, for example, stomach aches and bananas) as briefly described above. Alternatively, a sequential pattern may be determined for multiple subjective user states and multiple objective occurrences. Such a sequential pattern may particularly map the exact temporal or time sequencing of the various events (e.g., subjective user states and/or objective occurrences). The determined sequential pattern may then be used to provide useful information to the user and/or third parties.

The following is another illustrative example of how subjective user state data may be correlated with objective occurrence data by determining multiple sequential patterns and comparing the sequential patterns with each other. Suppose, for example, a user such as a microblogger reports that the user ate a banana on a Monday. The consumption of the banana, in this example, is a reported first objective occurrence associated with the user. The user then reports that 15 minutes after eating the banana, the user felt very happy. The reporting of the emotional state (e.g., felt very happy) is, in this example, a reported first subjective user state. Thus, the reported incidence of the first objective occurrence (e.g., eating the banana) and the reported incidence of the first subjective user state (user felt very happy) on Monday may be represented by a first sequential pattern.

On Tuesday, the user reports that the user ate another banana (e.g., a second objective occurrence associated with the user). The user then reports that 20 minutes after eating the second banana, the user felt somewhat happy (e.g., a second subjective user state). Thus, the reported incidence of the second objective occurrence (e.g., eating the second banana) and the reported incidence of the second subjective user state (user felt somewhat happy) on Tuesday may be represented by a second sequential pattern. Note that in this example, the occurrences of the first subjective user state and the second subjective user state may be indicated by subjective user state data while the occurrences of the first objective occurrence and the second objective occurrence may be indicated by objective occurrence data.

In a slight variation of the above example, suppose the user had forgotten to report for Tuesday the consumption of the banana but does report feeling somewhat happy on Tuesday. This may result in the user being asked, based on the reporting of the user feeling somewhat happy on Tuesday, as to whether the user ate anything prior to feeling somewhat happy or whether the user ate a banana prior to feeling somewhat happy. Asking of such questions may be prompted both in response to the reporting of the user feeling somewhat happy on Tuesday and on referencing historical data (e.g., first sequential pattern derived from Monday's consumption of banana and feeling happy). Upon the user confirming the consumption of the banana on Tuesday, a second sequential pattern may be determined.

In any event, by comparing the first sequential pattern with the second sequential pattern, the subjective user state data may be correlated with the objective occurrence data. In some implementations, the comparison of the first sequential pattern with the second sequential pattern may involve trying to match the first sequential pattern with the second sequential pattern by examining certain attributes and/or metrics. For example, comparing the first subjective user state (e.g., user felt very happy) of the first sequential pattern with the second subjective user state (e.g., user felt somewhat happy) of the second sequential pattern to see if they at least substantially match or are contrasting (e.g., being very happy in contrast to being slightly happy or being happy in contrast to being sad). Similarly, comparing the first objective occurrence (e.g., eating a banana) of the first sequential pattern may be compared to the second objective occurrence (e.g., eating of another banana) of the second sequential pattern to determine whether they at least substantially match or are contrasting.

A comparison may also be made to determine if the extent of time difference (e.g., 15 minutes) between the first subjective user state (e.g., user being very happy) and the first objective occurrence (e.g., user eating a banana) matches or are at least similar to the extent of time difference (e.g., 20 minutes) between the second subjective user state (e.g., user being somewhat happy) and the second objective occurrence (e.g., user eating another banana). These comparisons may be made in order to determine whether the first sequential pattern matches the second sequential pattern. A match or substantial match would suggest, for example, that a subjective user state (e.g., happiness) is linked to a particular objective occurrence (e.g., consumption of banana).

As briefly described above, the comparison of the first sequential pattern with the second sequential pattern may include a determination as to whether, for example, the respective subjective user states and the respective objective occurrences of the sequential patterns are contrasting subjective user states and/or contrasting objective occurrences. For example, suppose in the above example the user had reported that the user had eaten a whole banana on Monday and felt very energetic (e.g., first subjective user state) after eating the whole banana (e.g., first objective occurrence). Suppose that the user also reported that on Tuesday he ate a half a banana instead of a whole banana and only felt slightly energetic (e.g., second subjective user state) after eating the half banana (e.g., second objective occurrence). In this scenario, the first sequential pattern (e.g., feeling very energetic after eating a whole banana) may be compared to the second sequential pattern (e.g., feeling slightly energetic after eating only a half of a banana) to at least determine whether the first subjective user state (e.g., being very energetic) and the second subjective user state (e.g., being slightly energetic) are contrasting subjective user states. Another determination may also be made during the comparison to determine whether the first objective occurrence (eating a whole banana) is in contrast with the second objective occurrence (e.g., eating a half of a banana).

In doing so, an inference may be made that eating a whole banana instead of eating only a half of a banana makes the user happier or eating more banana makes the user happier. Thus, the word "contrasting" as used here with respect to subjective user states refers to subjective user states that are the same type of subjective user states (e.g., the subjective user states being variations of a particular type of subjective user states such as variations of subjective mental states). Thus, for example, the first subjective user state and the second subjective user state in the previous illustrative example are merely variations of subjective mental states (e.g., happiness). Similarly, the use of the word "contrasting" as used here with respect to objective occurrences refers to objective states that are the same type of objective occurrences (e.g., consumption of food such as banana).

As those skilled in the art will recognize, a stronger correlation between the subjective user state data and the objective occurrence data could be obtained if a greater number of sequential patterns (e.g., if there was a third sequential pattern, a fourth sequential pattern, and so forth, that indicated that the user became happy or happier whenever the user ate bananas) are used as a basis for the correlation. Note that for ease of explanation and illustration, each of the exemplary sequential patterns to be described herein will be depicted as a sequential pattern of an occurrence of a single subjective user state and an occurrence of a single objective occurrence. However, those skilled in the art will recognize that a sequential pattern, as will be described herein, may also be associated with occurrences of multiple objective occurrences and/or multiple subjective user states. For example, suppose the user had reported that after eating a banana, he had gulped down a can of soda. The user then reported that he became happy but had an upset stomach. In this example, the sequential pattern associated with this scenario will be associated with two objective occurrences (e.g., eating a banana and drinking a can of soda) and two subjective user states (e.g., user having an upset stomach and feeling happy).

In some embodiments, and as briefly described earlier, the sequential patterns derived from subjective user state data and objective occurrence data may be based on temporal relationships between objective occurrences and subjective user states. For example, whether a subjective user state occurred before, after, or at least partially concurrently with an objective occurrence. For instance, a plurality of sequential patterns derived from subjective user state data and objective occurrence data may indicate that a user always has a stomach ache (e.g., subjective user state) after eating a banana (e.g., first objective occurrence).

Figure 1B:
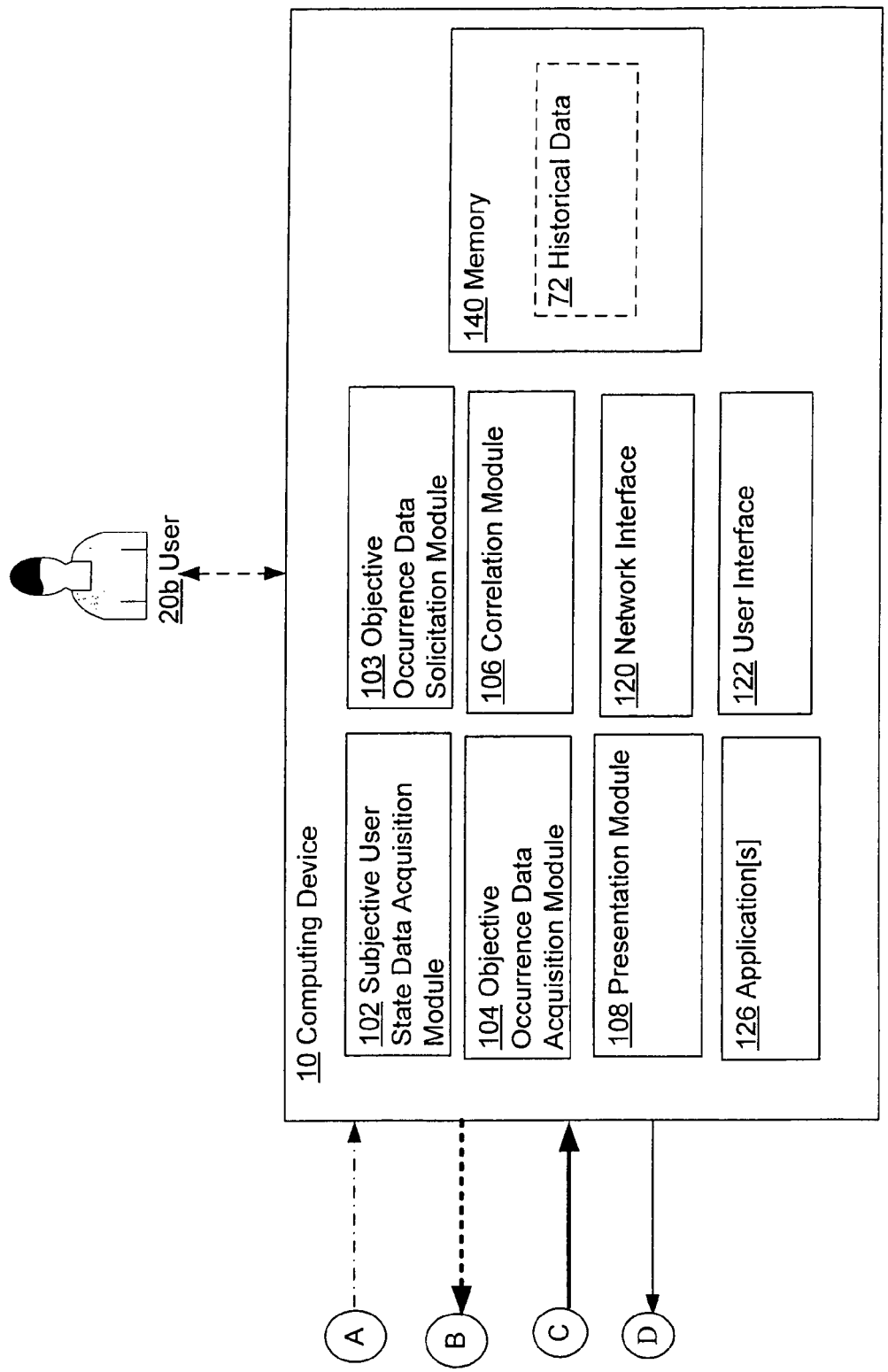

FIGS. 1a and 1b illustrate an example environment in accordance with various embodiments. In the illustrated environment, an exemplary system 100 may include at least a computing device 10 (see FIG. 1b) that may be employed in order to, among other things, acquire subjective user state data 60 associated with a user 20*, solicit and acquire objective occurrence data 70* in response to the acquisition of the subjective user state data 60, and to correlate the subjective user state data 60 with the objective occurrence data 70*. Note that in the following, "*" indicates a wildcard. Thus, user 20* may indicate a user 20a or a user 20b of FIGS. 1a and 1b.

In some embodiments, the computing device 10 may be a network server in which case the computing device 10 may communicate with a user 20a via a mobile device 30 and through a wireless and/or wired network 40. A network server, as will be described herein, may be in reference to a server located at a single network site or located across multiple network sites or a conglomeration of servers located at multiple network sites. The mobile device 30 may be a variety of computing/communication devices including, for example, a cellular phone, a personal digital assistant (PDA), a laptop, a desktop, or other types of computing/communication device that can communicate with the computing device 10.

In alternative embodiments, the computing device 10 may be a local computing device that communicates directly with a user 20b. For these embodiments, the computing device 10 may be any type of handheld device such as a cellular telephone, a PDA, or other types of computing/communication devices such as a laptop computer, a desktop computer, and so forth. In various embodiments, the computing device 10 may be a peer-to-peer network component device. In some embodiments, the computing device 10 may operate via a web 2.0 construct.

In embodiments where the computing device 10 is a server, the computing device 10 may obtain the subjective user state data 60 indirectly from a user 20a via a network interface 120. In alternative embodiments in which the computing device 10 is a local device such as a handheld device (e.g., cellular telephone, personal digital assistant, etc.), the subjective user state data 60 may be directly obtained from a user 20b via a user interface 122. As will be further described, the computing device 10 may acquire the objective occurrence data 70* from one or more alternative sources.

For ease of illustration and explanation, the following systems and operations to be described herein will be generally described in the context of the computing device 10 being a network server. However, those skilled in the art will recognize that these systems and operations may also be implemented when the computing device 10 is a local device such as a handheld device that may communicate directly with a user 20b.

Assuming that the computing device 10 is a server, the computing device 10, in various implementations, may be configured to acquire subjective user state data 60 including data indicating at least one subjective user state 60a via the mobile device 30 and through wireless and/or wired networks 40. In some implementations, the subjective user state data 60 may further include additional data that may indicate one or more additional subjective user states (e.g., data indicating at least a second subjective user state 60b).

In various embodiments, the data indicating the at least one subjective user state 60a, as well as the data indicating the at least second subjective user state 60b, may be in the form of blog entries, such as microblog entries, status reports (e.g., social networking status reports), electronic messages (email, text messages, instant messages, etc.) or other types of electronic messages or documents. The data indicating the at least one subjective user state 60a and the data indicating the at least second subjective user state 60b may, in some instances, indicate the same, contrasting, or completely different subjective user states.

Examples of subjective user states that may be indicated by the subjective user state data 60 include, for example, subjective mental states of the user 20a (e.g., user 20a is sad or angry), subjective physical states of the user 20a (e.g., physical or physiological characteristic of the user 20a such as the presence, absence, elevating, or easing of a stomach ache or headache), subjective overall states of the user 20a (e.g., user 20a is "well"), and/or other subjective user states that only the user 20a can typically indicate.

The computing device 10 may also be configured to solicit objective occurrence data 70* including data indicating at least one objective occurrence. Such a solicitation of the objective occurrence data 70* may be prompted in response to the acquisition of subjective user state data 60 and/or in response to referencing of historical data 72 as will be further described herein. The solicitation of objective occurrence data 70* may be made through a network interface 120 or through the user interface 122. As will be further described, the solicitation of the objective occurrence data 70* from a source (e.g., the user 20*, one or more third party sources, or one or more sensors 35) may be accomplished in a number of ways depending on the specific circumstances (e.g., whether the computing device 10 is a server or a local device and whether the source is the user 20*, one or more third parties 50, or one or more sensors 35). Examples of how objective occurrence data 70* could be solicited include, for example, transmitting via a network interface 120 a request for objective occurrence data 70*, indicating via a user interface 122 a request for objective occurrence data 70*, configurating or activating one or more sensors 35 to collect and provide objective occurrence data 70b, and so forth.

After soliciting for the objective occurrence data 70*, the computing device 10 may be configured to acquire the objective occurrence data 70* from one or more sources. In various embodiments, the objective occurrence data 70* acquired by the computing device 10 may include data indicative of at least one objective occurrence associated with a user 20a (or with user 20b in the case where the computing device 10 is a local device). The objective occurrence data 70* may additionally include data indicative of one or more additional objective occurrences associated with the user 20a (or user 20b) including data indicating at least a second objective occurrence associated with the user 20a (or user 20b). In some embodiments, objective occurrence data 70a may be acquired from one or more third parties 50. Examples of third parties 50 include, for example, other users (not depicted), a healthcare provider, a hospital, a place of employment, a content provider, and so forth.

In some embodiments, objective occurrence data 70b may be acquired from one or more sensors 35 that may be designed for sensing or monitoring various aspects associated with the user 20a (or user 20b). For example, in some implementations, the one or more sensors 35 may include a global positioning system (GPS) device for determining the location of the user 20a and/or a physical activity sensor for measuring physical activities of the user 20a. Examples of a physical activity sensor include, for example, a pedometer for measuring physical activities of the user 20a. In certain implementations, the one or more sensors 35 may include one or more physiological sensor devices for measuring physiological characteristics of the user 20a. Examples of physiological sensor devices include, for example, a blood pressure monitor, a heart rate monitor, a glucometer, and so forth. In some implementations, the one or more sensors 35 may include one or more image capturing devices such as a video or digital camera.

In some embodiments, objective occurrence data 70c may be acquired from the user 20a via the mobile device 30 (or from user 20b via user interface 122). For these embodiments, the objective occurrence data 70c may be in the form of blog entries (e.g., microblog entries), status reports, or other types of electronic entries or messages. In various implementations, the objective occurrence data 70c acquired from the user 20a may indicate, for example, activities (e.g., exercise or food or medicine intake) performed by the user 20a, certain physical characteristics (e.g., blood pressure or location) associated with the user 20a, or other aspects associated with the user 20a that the user 20a can report objectively. The objective occurrence data 70c may be in the form of a text data, audio or voice data, or image data.

After acquiring the subjective user state data 60 and the objective occurrence data 70*, the computing device 10 may be configured to correlate the acquired subjective user data 60 with the acquired objective occurrence data 70* by, for example, determining whether there is a sequential relationship between the one or more subjective user states as indicated by the acquired subjective user state data 60 and the one or more objective occurrences indicated by the acquired objective occurrence data 70*.

In some embodiments, and as will be further indicated in the operations and processes to be described herein, the computing device 10 may be further configured to present one or more results of correlation. In various embodiments, the one or more correlation results 80 may be presented to the user 20a and/or to one or more third parties 50 in various forms (e.g., in the form of an advisory, a warning, a prediction, and so forth). The one or more third parties 50 may be other users 20* such as other microbloggers, a health care provider, advertisers, and/or content providers.

As illustrated in FIG. 1b, computing device 10 may include one or more components and/or sub-modules. For instance, in various embodiments, computing device 10 may include a subjective user state data acquisition module 102, an objective occurrence data solicitation module 103, an objective occurrence data acquisition module 104, a correlation module 106, a presentation module 108, a network interface 120 (e.g., network interface card or NIC), a user interface 122 (e.g., a display monitor, a touchscreen, a keypad or keyboard, a mouse, an audio system including a microphone and/or speakers, an image capturing system including digital and/or video camera, and/or other types of interface devices), one or more applications 126 (e.g., a web 2.0 application, a voice recognition application, and/or other applications), and/or memory 140, which may include historical data 72.

FIG. 2a illustrates particular implementations of the subjective user state data acquisition module 102 of the computing device 10 of FIG. 1b. In brief, the subjective user state data acquisition module 102 may be designed to, among other things, acquire subjective user state data 60 including data indicating at least one subjective user state 60a. As further illustrated, the subjective user state data acquisition module 102 may include a subjective user state data reception module 202 for receiving the subjective user state data 60 from a user 20a via the network interface 120 (e.g., in the case where the computing device 10 is a network server). Alternatively, the subjective user state data reception module 202 may receive the subjective user state data 60 directly from a user 20b (e.g., in the case where the computing device 10 is a local device) via the user interface 122.

In some implementations, the subjective user state data reception module 202 may further include a user interface data reception module 204 and/or a network interface data reception module 206. In brief, and as will be further described in the processes and operations to be described herein, the user interface data reception module 204 may be configured to acquire subjective user state data 60 via a user interface 122 (e.g., a display monitor, a keyboard, a touch screen, a mouse, a keypad, a microphone, a camera, and/or other interface devices) such as in the case where the computing device 10 is a local device to be used directly by a user 20b. In contrast, the network interface data reception module 206 may be configured to acquire subjective user state data 60 from a wireless and/or wired network 40 via a network interface 120 (e.g., network interface card or NIC) such as in the case where the computing device 10 is a network server.

In various embodiments, the subjective user state data acquisition module 102 may include a time data acquisition module 208 for acquiring time and/or temporal elements associated with one or more subjective user states of a user 20*. For these embodiments, the time and/or temporal elements (e.g., time stamps, time interval indicators, and/or temporal relationship indicators) acquired by the time data acquisition module 208 may be useful for, among other things, determining one or more sequential patterns associated with subjective user states and objective occurrences as will be further described herein. In some implementations, the time data acquisition module 208 may include a time stamp acquisition module 210 for acquiring (e.g., either by receiving or generating) one or more time stamps associated with one or more subjective user states. In the same or different implementations, the time data acquisition module 208 may include a time interval acquisition module 212 for acquiring (e.g., either by receiving or generating) indications of one or more time intervals associated with one or more subjective user states. In the same or different implementations, the time data acquisition module 208 may include a temporal relationship acquisition module 214 for acquiring, for example, indications of temporal relationships between subjective user states and objective occurrences. For example, acquiring an indication that a subjective user state such as a stomach ache occurred before, after, or at least partially concurrently with incidence of an objective occurrence such as eating lunch or the time being noon.

FIG. 2b illustrates particular implementations of the objective occurrence data solicitation module 103 of the computing device 10 of FIG. 1b. The objective occurrence data solicitation module 103 may be configured or designed to solicit, in response to acquisition of subjective user state data 60 including data indicating at least subjective user state 60a, objective occurrence data 70* including data indicating at least one objective occurrence. The objective occurrence data 70* to be solicited may be requested from a user 20*, from one or more third parties 50 (e.g., third party sources such as other users (not depicted), content providers, healthcare entities including doctor's or dentist offices and hospitals, and so forth), or may be solicited from one or more sensors 35. The solicitation may be made via, for example, network interface 120 or via the user interface 122 in the case where user 20b is the source for the objective occurrence data 70*.

In various embodiments, the objective occurrence data solicitation module 103 may be configured to solicit data indicating occurrence of at least one objective occurrence that occurred at a specified point in time or occurred at a specified time interval. In some implementations, the solicitation of the objective occurrence data 70* by the objective occurrence data solicitation module 103 may be prompted by the acquisition of subjective user state data 60 including data indicating at least one subjective user state 60a and/or as a result of referencing historical data 72 (which may be stored in memory 140). Historical data 72, in some instances, may prompt solicitation of particular data indicating occurrence of a particular or a particular type of objective occurrence. In some implementations, the historical data 72 to be referenced may be historical data 72 indicative of a link between a subjective user state type and an objective occurrence type. In the same or different implementations, the historical data 72 to be referenced may include one or more historical sequential patterns associated with the user 20*, a group of users, or the general population. In the same or different implementations, the historical data 72 to be referenced may include historical medical data associated with the user 20*, associated with other users, or associated with the general population. The relevance of the historical data 72 with respect to the solicitation operations performed by the objective occurrence data solicitation module 103 will be apparent in the processes and operations to be described herein.

In order to perform the various functions described herein, the objective occurrence data solicitation module 103 may include a network interface solicitation module 215, a user interface solicitation module 216, a requesting module 217, a configuration module 218, and/or a directing/instructing module 219. In brief, the network interface solicitation module 215 may be employed in order to solicit objective occurrence data 70* via a network interface 120. The user interface solicitation module 216 may be employed in order to, among other things, solicit objective occurrence data 70* via user interface 122 from, for example, a user 20b. The requesting module 217 may be employed in order to request the objective occurrence data 70a and 70b from a user 20* or from one or more third parties 50. The configuration module 218 may be employed in order to configure one or more sensors 35 to collect and provide objective occurrence data 70b. The directing/instructing module 219 may be employed in order to direct and/or instruct the one or more sensors 35 to collect and provide objective occurrence data 70b.

Figure 2C:
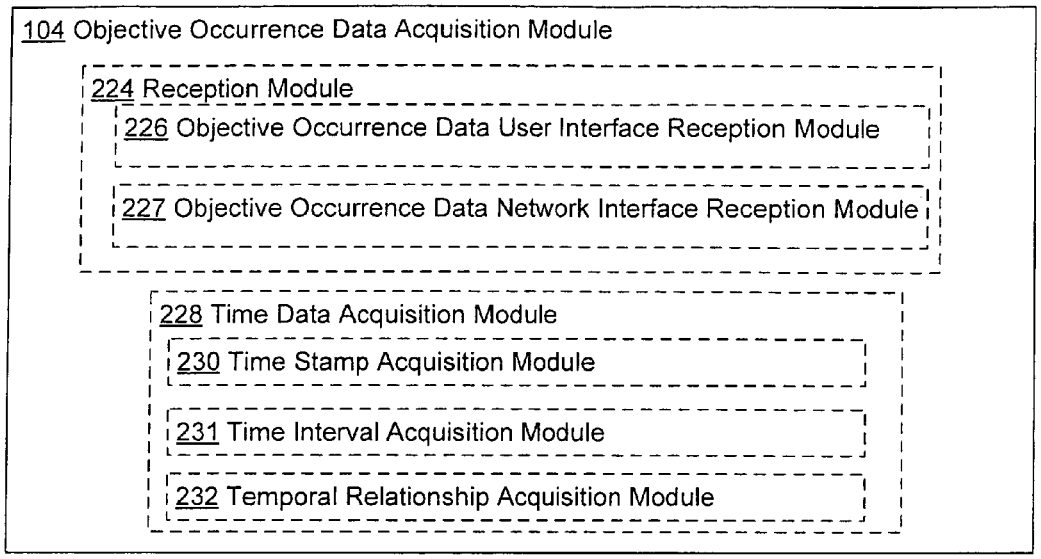
FIG. 2c shows another perspective of the objective occurrence data acquisition module 104 of the computing device 10 of FIG. 1b.

Referring now to FIG. 2c illustrating particular implementations of the objective occurrence data acquisition module 104 of the computing device 10 of FIG. 1b. In various implementations, the objective occurrence data acquisition module 104 may be configured to acquire (e.g., receive from a user 20*, receive from one or more third parties 50, or receive from one or more sensors 35) objective occurrence data 70* including data indicative of one or more objective occurrences that may be associated with a user 20*. In various embodiments, the objective occurrence data acquisition module 104 may include a reception module 224 configured to receive objective occurrence data 70*. In some embodiments, the reception module 224 may further include an objective occurrence data user interface reception module 226 for receiving, via a user interface 122, objective occurrence data 70* including data indicating at least one objective occurrence from a user 20b. In the same or different embodiments, the reception module 224 may include an objective occurrence data network interface reception module 227 for receiving, via a network interface 120, objective occurrence data including data indicating at least one objective occurrence from a user 20b, from one or more third parties 50, or from one or more sensors 35.

In various embodiments, the objective occurrence data acquisition module 104 may include a time data acquisition module 228 configured to acquire (e.g., receive or generate) time and/or temporal elements associated with one or more objective occurrences. For these embodiments, the time and/or temporal elements (e.g., time stamps, time intervals, and/or temporal relationships) may be useful for determining sequential patterns associated with objective occurrences and subjective user states.

In some implementations, the time data acquisition module 228 may include a time stamp acquisition module 230 for acquiring (e.g., either by receiving or by generating) one or more time stamps associated with one or more objective occurrences associated with a user 20*. In the same or different implementations, the time data acquisition module 228 may include a time interval acquisition module 231 for acquiring (e.g., either by receiving or generating) indications of one or more time intervals associated with one or more objective occurrences. In the same or different implementations, the time data acquisition module 228 may include a temporal relationship acquisition module 232 for acquiring indications of temporal relationships between objective occurrences and subjective user states (e.g., an indication that an objective occurrence occurred before, after, or at least partially concurrently with incidence of a subjective user state).

Figure 2E:
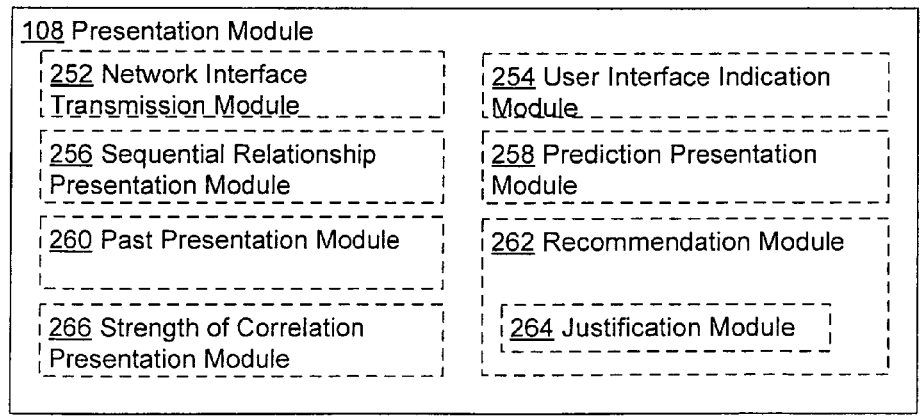
FIG. 2e shows another perspective of the presentation module 108 of the computing device 10 of FIG. 1b.
Figure 2F:
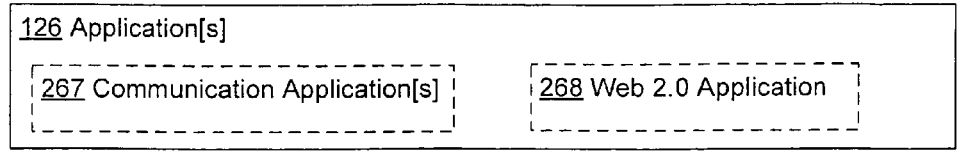
FIG. 2f shows another perspective of the one or more applications 126 of the computing device 10 of FIG. 1b.
Figure 2D:
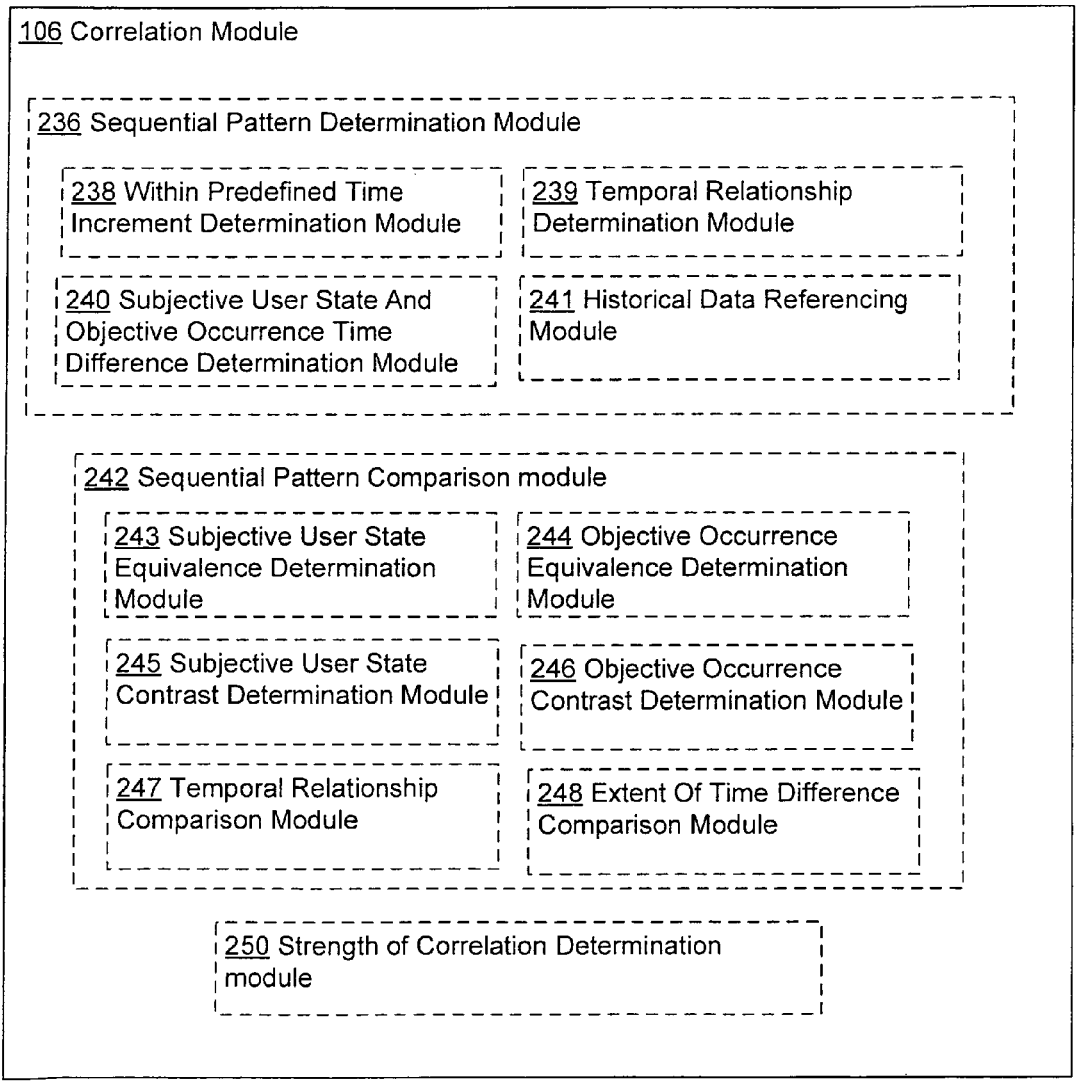
FIG. 2d shows another perspective of the correlation module 106 of the computing device 10 of FIG. 1b.

Turning now to FIG. 2d illustrating particular implementations of the correlation module 106 of the computing device 10 of FIG. 1b. The correlation module 106 may be configured to, among other things, correlate subjective user state data 60 with objective occurrence data 70* based, at least in part, on a determination of at least one sequential pattern of at least one objective occurrence and at least one subjective user state. In various embodiments, the correlation module 106 may include a sequential pattern determination module 236 configured to determine one or more sequential patterns of one or more subjective user states and one or more objective occurrences.

The sequential pattern determination module 236, in various implementations, may include one or more sub-modules that may facilitate in the determination of one or more sequential patterns. As depicted, the one or more sub-modules that may be included in the sequential pattern determination module 236 may include, for example, a "within predefined time increment determination" module 238, a temporal relationship determination module 239, a subjective user state and objective occurrence time difference determination module 240, and/or a historical data referencing module 241. In brief, the within predefined time increment determination module 238 may be configured to determine whether at least one subjective user state of a user 20* occurred within a predefined time increment from an incidence of at least one objective occurrence. For example, determining whether a user 20* feeling "bad" (i.e., a subjective user state) occurred within ten hours (i.e., predefined time increment) of eating a large chocolate sundae (i.e., an objective occurrence). Such a process may be used in order to filter out events that are likely not related or to facilitate in determining the strength of correlation between subjective user state data 60 and objective occurrence data 70*.

The temporal relationship determination module 239 may be configured to determine the temporal relationships between one or more subjective user states and one or more objective occurrences. For example, this may entail determining whether a particular subjective user state (e.g., sore back)

occurred before, after, or at least partially concurrently with incidence of an objective occurrence (e.g., sub-freezing temperature).

The subjective user state and objective occurrence time difference determination module 240 may be configured to determine the extent of time difference between the incidence of at least one subjective user state and the incidence of at least one objective occurrence. For example, determining how long after taking a particular brand of medication (e.g., objective occurrence) did a user 20* feel "good" (e.g., subjective user state).

The historical data referencing module 241 may be configured to reference historical data 72 in order to facilitate in determining sequential patterns. For example, in various implementations, the historical data 72 that may be referenced may include, for example, general population trends (e.g., people having a tendency to have a hangover after drinking or ibuprofen being more effective than aspirin for toothaches in the general population), medical information such as genetic, metabolome, or proteome information related to the user 20* (e.g., genetic information of the user 20* indicating that the user 20* is susceptible to a particular subjective user state in response to occurrence of a particular objective occurrence), or historical sequential patterns such as known sequential patterns of the general population or of the user 20* (e.g., people tending to have difficulty sleeping within five hours after consumption of coffee). In some instances, such historical data 72 may be useful in associating one or more subjective user states with one or more objective occurrences.

In some embodiments, the correlation module 106 may include a sequential pattern comparison module 242. As will be further described herein, the sequential pattern comparison module 242 may be configured to compare two or more sequential patterns with each other to determine, for example, whether the sequential patterns at least substantially match each other or to determine whether the sequential patterns are contrasting sequential patterns.

As depicted in FIG. 2d, in various implementations, the sequential pattern comparison module 242 may further include one or more sub-modules that may be employed in order to, for example, facilitate in the comparison of different sequential patterns. For example, in various implementations, the sequential pattern comparison module 242 may include one or more of a subjective user state equivalence determination module 243, an objective occurrence equivalence determination module 244, a subjective user state contrast determination module 245, an objective occurrence contrast determination module 246, a temporal relationship comparison module 247, and/or an extent of time difference comparison module 248.

The subjective user state equivalence determination module 243 may be configured to determine whether subjective user states associated with different sequential patterns are equivalent. For example, the subjective user state equivalence determination module 243 may determine whether a first subjective user state of a first sequential pattern is equivalent to a second subjective user state of a second sequential pattern. For instance, suppose a user 20* reports that on Monday he had a stomach ache (e.g., first subjective user state) after eating at a particular restaurant (e.g., a first objective occurrence), and suppose further that the user 20* again reports having a stomach ache (e.g., a second subjective user state) after eating at the same restaurant (e.g., a second objective occurrence) on Tuesday, then the subjective user state equivalence determination module 243 may be employed in order to compare the first subjective user state (e.g., stomach ache) with the second subjective user state (e.g., stomach ache) to determine whether they are equivalent.

In contrast, the objective occurrence equivalence determination module 244 may be configured to determine whether objective occurrences of different sequential patterns are equivalent. For example, the objective occurrence equivalence determination module 244 may determine whether a first objective occurrence of a first sequential pattern is equivalent to a second objective occurrence of a second sequential pattern. For instance, for the above example the objective occurrence equivalence determination module 244 may compare eating at the particular restaurant on Monday (e.g., first objective occurrence) with eating at the same restaurant on Tuesday (e.g., second objective occurrence) in order to determine whether the first objective occurrence is equivalent to the second objective occurrence.

In some implementations, the sequential pattern comparison module 242 may include a subjective user state contrast determination module 245 that may be configured to determine whether subjective user states associated with different sequential patterns are contrasting subjective user states. For example, the subjective user state contrast determination module 245 may determine whether a first subjective user state of a first sequential pattern is a contrasting subjective user state from a second subjective user state of a second sequential pattern. To illustrate, suppose a user 20* reports that he felt very "good" (e.g., first subjective user state) after jogging for an hour (e.g., first objective occurrence) on Monday, but reports that he felt "bad" (e.g., second subjective user state) when he did not exercise (e.g., second objective occurrence) on Tuesday, then the subjective user state contrast determination module 245 may compare the first subjective user state (e.g., feeling good) with the second subjective user state (e.g., feeling bad) to determine that they are contrasting subjective user states.

In some implementations, the sequential pattern comparison module 242 may include an objective occurrence contrast determination module 246 that may be configured to determine whether objective occurrences of different sequential patterns are contrasting objective occurrences. For example, the objective occurrence contrast determination module 246 may determine whether a first objective occurrence of a first sequential pattern is a contrasting objective occurrence from a second objective occurrence of a second sequential pattern. For instance, for the above example, the objective occurrence contrast determination module 246 may compare the "jogging" on Monday (e.g., first objective occurrence) with the "no jogging" on Tuesday (e.g., second objective occurrence) in order to determine whether the first objective occurrence is a contrasting objective occurrence from the second objective occurrence. Based on the contrast determination, an inference may be made that the user 20* may feel better by jogging rather than by not jogging at all.

In some embodiments, the sequential pattern comparison module 242 may include a temporal relationship comparison module 247 that may be configured to make comparisons between different temporal relationships of different sequential patterns. For example, the temporal relationship comparison module 247 may compare a first temporal relationship between a first subjective user state and a first objective occurrence of a first sequential pattern with a second temporal relationship between a second subjective user state and a second objective occurrence of a second sequential pattern in order to determine whether the first temporal relationship at least substantially matches the second temporal relationship.

For example, suppose in the above example the user 20* eating at the particular restaurant (e.g., first objective occurrence) and the subsequent stomach ache (e.g., first subjective user state) on Monday represents a first sequential pattern while the user 20* eating at the same restaurant (e.g., second objective occurrence) and the subsequent stomach ache (e.g., second subjective user state) on Tuesday represents a second sequential pattern. In this example, the occurrence of the stomach ache after (rather than before or concurrently) eating at the particular restaurant on Monday represents a first temporal relationship associated with the first sequential pattern while the occurrence of a second stomach ache after (rather than before or concurrently) eating at the same restaurant on Tuesday represents a second temporal relationship associated with the second sequential pattern. Under such circumstances, the temporal relationship comparison module 247 may compare the first temporal relationship to the second temporal relationship in order to determine whether the first temporal relationship and the second temporal relationship at least substantially match (e.g., stomachaches in both temporal relationships occurring after eating at the restaurant). Such a match may result in the inference that a stomach ache is associated with eating at the particular restaurant.

In some implementations, the sequential pattern comparison module 242 may include an extent of time difference comparison module 248 that may be configured to compare the extent of time differences between incidences of subjective user states and incidences of objective occurrences of different sequential patterns. For example, the extent of time difference comparison module 248 may compare the extent of time difference between incidence of a first subjective user state and incidence of a first objective occurrence of a first sequential pattern with the extent of time difference between incidence of a second subjective user state and incidence of a second objective occurrence of a second sequential pattern. In some implementations, the comparisons may be made in order to determine that the extent of time differences of the different sequential patterns at least substantially or proximately match.

In some embodiments, the correlation module 106 may include a strength of correlation determination module 250 for determining a strength of correlation between subjective user state data 60 and objective occurrence data 70* associated with a user 20*. In some implementations, the strength of correlation may be determined based, at least in part, on the results provided by the other sub-modules of the correlation module 106 (e.g., the sequential pattern determination module 236, the sequential pattern comparison module 242, and their sub-modules).

FIG. 2e illustrates particular implementations of the presentation module 108 of the computing device 10 of FIG. 1b. In various implementations, the presentation module 108 may be configured to present, for example, one or more results of the correlation operations performed by the correlation module 106. The one or more results may be presented in different ways in various alternative embodiments. For example, in some implementations, the presentation of the one or more results may entail the presentation module 108 presenting to the user 20* (or some other third party 50) an indication of a sequential relationship between a subjective user state and an objective occurrence associated with the user 20* (e.g., "whenever you eat a banana, you have a stomach ache). In alternative implementations, other ways of presenting the results of the correlation may be employed. For example, in various alternative implementations, a notification may be provided to notify past tendencies or patterns associated with a user 20*. In some implementations, a notification of a possible future outcome may be provided. In other implementations, a recommendation for a future course of action based on past patterns may be provided. These and other ways of presenting the correlation results will be described in the processes and operations to be described herein.

In various implementations, the presentation module 108 may include a network interface transmission module 252 for transmitting one or more results of the correlation performed by the correlation module 106 via network interface 120. For example, in the case where the computing device 10 is a server, the network interface transmission module 252 may be configured to transmit to the user 20a or a third party 50 the one or more results of the correlation performed by the correlation module 106 via a network interface 120.

In the same or different implementations, the presentation module 108 may include a user interface indication module 254 for indicating the one or more results of the correlation operations performed by the correlation module 106 via a user interface 122. For example, in the case where the computing device 10 is a local device, the user interface indication module 254 may be configured to indicate to a user 20b the one or more results of the correlation performed by the correlation module 106 via a user interface 122 (e.g., a display monitor, a touchscreen, an audio system including at least a speaker, and/or other interface devices).

The presentation module 108 may further include one or more sub-modules to present the one or more results of the correlation operations performed by the correlation module 106 in different forms. For example, in some implementations, the presentation module 108 may include a sequential relationship presentation module 256 configured to present an indication of a sequential relationship between at least one subjective user state of a user 20* and at least one objective occurrence. In the same or different implementations, the presentation module 108 may include a prediction presentation module 258 configured to present a prediction of a future subjective user state of a user 20* resulting from a future objective occurrence associated with the user 20*. In the same or different implementations, the prediction presentation module 258 may also be designed to present a prediction of a future subjective user state of a user 20* resulting from a past objective occurrence associated with the user 20*. In some implementations, the presentation module 108 may include a past presentation module 260 that is designed to present a past subjective user state of a user 20* in connection with a past objective occurrence associated with the user 20*.

In some implementations, the presentation module 108 may include a recommendation module 262 that is configured to present a recommendation for a future action based, at least in part, on the results of a correlation of subjective user state data 60 with objective occurrence data 70* performed by the correlation module 106. In certain implementations, the recommendation module 262 may further include a justification module 264 for presenting a justification for the recommendation presented by the recommendation module 262. In some implementations, the presentation module 108 may include a strength of correlation presentation module 266 for presenting an indication of a strength of correlation between subjective user state data 60 and objective occurrence data 70*.

In various embodiments, the computing device 10 may include a network interface 120 that may facilitate in communicating with a user 20a, one or more sensors 35, and/or one or more third parties 50. For example, in embodiments where the computing device 10 is a server, the computing device 10 may include a network interface 120 that may be configured to receive from the user 20a subjective user state data 60. In some embodiments, objective occurrence data 70a, 70b, and/or 70c may also be received through the network interface 120. Examples of a network interface 120 includes, for example, a network interface card (NIC).

The computing device 10, in various embodiments, may also include a memory 140 for storing various data. For example, in some embodiments, memory 140 may be employed in order to store historical data 72. In some implementations, the historical data 72 may include historical subjective user state data of a user 20* that may indicate one or more past subjective user states of the user 20* and historical objective occurrence data that may indicate one or more past objective occurrences. In same or different implementations, the historical data 72 may include historical medical data of a user 20* (e.g., genetic, metoblome, proteome information), population trends, historical sequential patterns derived from general population, and so forth.

In various embodiments, the computing device 10 may include a user interface 122 to communicate directly with a user 20b. For example, in embodiments in which the computing device 10 is a local device such as a handheld device (e.g., cellular telephone, PDA, and so forth), the user interface 122 may be configured to directly receive from the user 20b subjective user state data 60. The user interface 122 may include, for example, one or more of a display monitor, a touch screen, a key board, a key pad, a mouse, an audio system, an imaging system including a digital or video camera, and/or other user interface devices.

FIG. 2e illustrates particular implementations of the one or more applications 126 of FIG. 1b. For these implementations, the one or more applications 126 may include, for example, one or more communication applications 267 such as a text messaging application and/or an audio messaging application including a voice recognition system application. In some implementations, the one or more applications 126 may include a web 2.0 application 268 to facilitate communication via, for example, the World Wide Web. The functional roles of the various components, modules, and sub-modules of the computing device 10 presented thus far will be described in greater detail with respect to the processes and operations to be described herein. Note that the subjective user state data 60 may be in a variety of forms including, for example, text messages (e.g., blog entries, microblog entries, instant messages, text email messages, and so forth), audio messages, and/or images (e.g., an image capturing user's facial expression or gestures).

Figure 3:
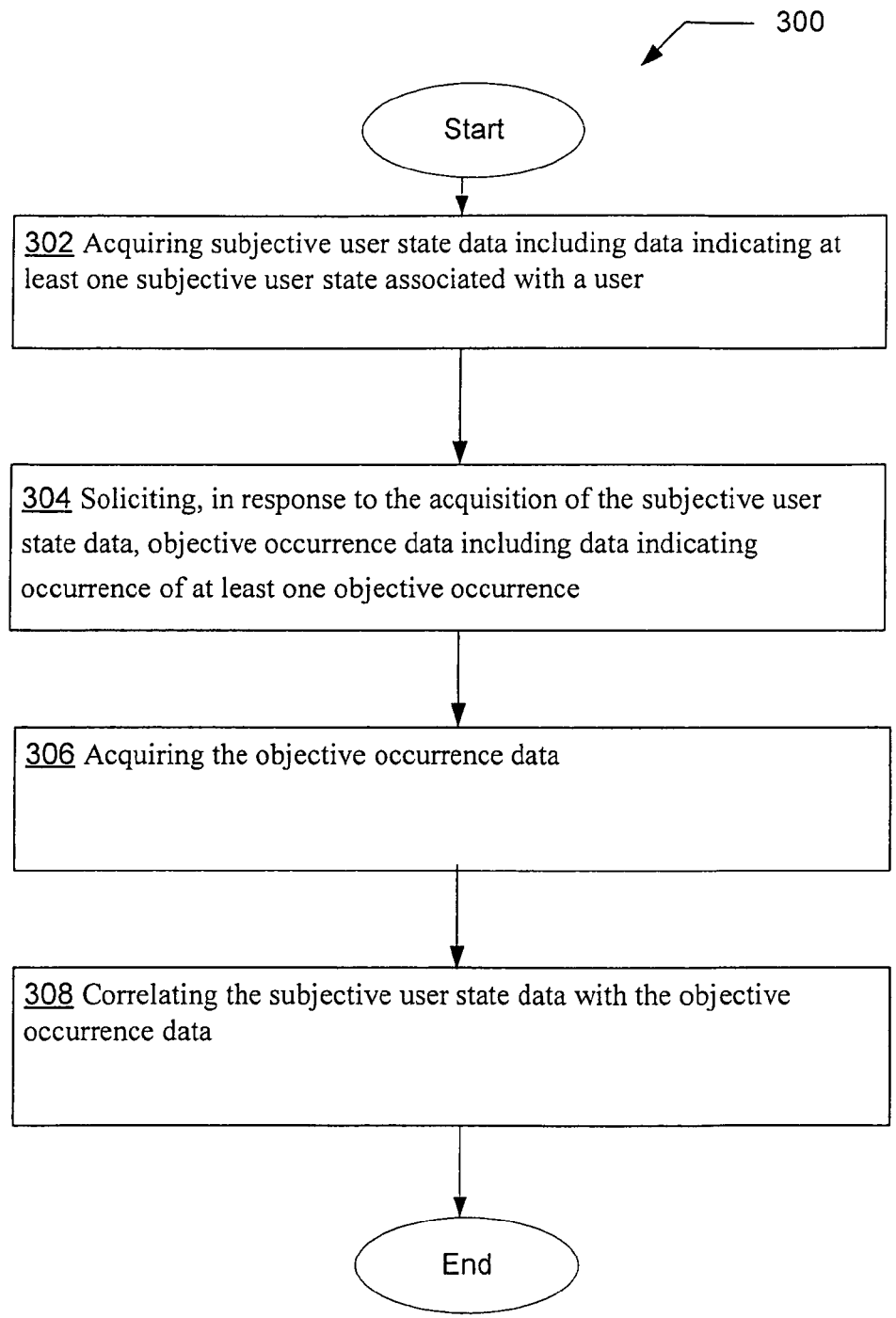
FIG. 3 is a high-level logic flowchart of a process.

FIG. 3 illustrates an operational flow 300 representing example operations related to, among other things, acquisition and correlation of subjective user state data 60 and objective occurrence data 70* in accordance with various embodiments. In some embodiments, the operational flow 300 may be executed by, for example, the computing device 10 of FIG. 1b.

In FIG. 3 and in the following figures that include various examples of operational flows, discussions and explanations may be provided with respect to the above-described exemplary environment of FIGS. 1a and 1b, and/or with respect to other examples (e.g., as provided in FIGS. 2a-2f) and contexts. However, it should be understood that the operational flows may be executed in a number of other environments and contexts, and/or in modified versions of FIGS. 1a, 1b, and 2a-2f. Also, although the various operational flows are presented in the sequence(s) illustrated, it should be understood that the various operations may be performed in other orders than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a subjective user state data acquisition operation 302 for acquiring subjective user state data including data indicating at least one subjective user state associated with a user. For instance, the subjective user state data acquisition module 102 of the computing device 10 of FIG. 1b acquiring (e.g., receiving via network interface 120 or via user interface 122) subjective user state data 60 including data indicating at least one subjective user state 60a (e.g., a subjective mental state, a subjective physical state, or a subjective overall state) associated with a user 20*.

Operational flow 300 may also include an objective occurrence data solicitation operation 304 for soliciting, in response to the acquisition of the subjective user state data, objective occurrence data including data indicating occurrence of at least one objective occurrence. For instance, the objective occurrence data solicitation module 103 of the computing device 10 soliciting (e.g., from the user 20*, from one or more third parties 50, or from one or more sensors 35), in response to the acquisition of the subjective user state data 60, objective occurrence data 70* including data indicating occurrence of at least one objective occurrence 60a (e.g., ingestion of a food, medicine, or nutraceutical). Note that the solicitation of the objective occurrence data as described above does not necessarily mean, although it may in some cases, to solicitation of particular data that indicates occurrence of a particular or particular type of objective occurrence.

The term "soliciting" as used above may be in reference to direct or indirect solicitation of objective occurrence data 70* from one or more sources (e.g., user 20*, one or more sensors 35, or one or more third parties 50). For example, if the computing device 10 is a server, then the computing device 10 may indirectly solicit the objective occurrence data 70* from, for example, a user 20a by transmitting the solicitation (e.g., a request or inquiry) for the objective occurrence data 70* to the mobile device 30, which may then actually solicit the objective occurrence data 70* from the user 20a.

Operational flow 300 may further include an objective occurrence data acquisition operation 306 for acquiring the objective occurrence data. For instance, the objective occurrence data acquisition module 104 of the computing device 10 acquiring (e.g., receiving via user interface 122 or via the network interface 120) the objective occurrence data 70*.

Finally, operational flow 300 may include a correlation operation 308 for correlating the subjective user state data with the objective occurrence data. For instance, the correlation module 106 of the computing device 10 correlating the subjective user state data 60 with the objective occurrence data 70* by determining, for example, at least one sequential pattern (e.g., time sequential pattern) associated with the at least one subjective user state (e.g., user feeling "tired") and the at least one objective occurrence (e.g., high blood sugar level).

Figure 4A:
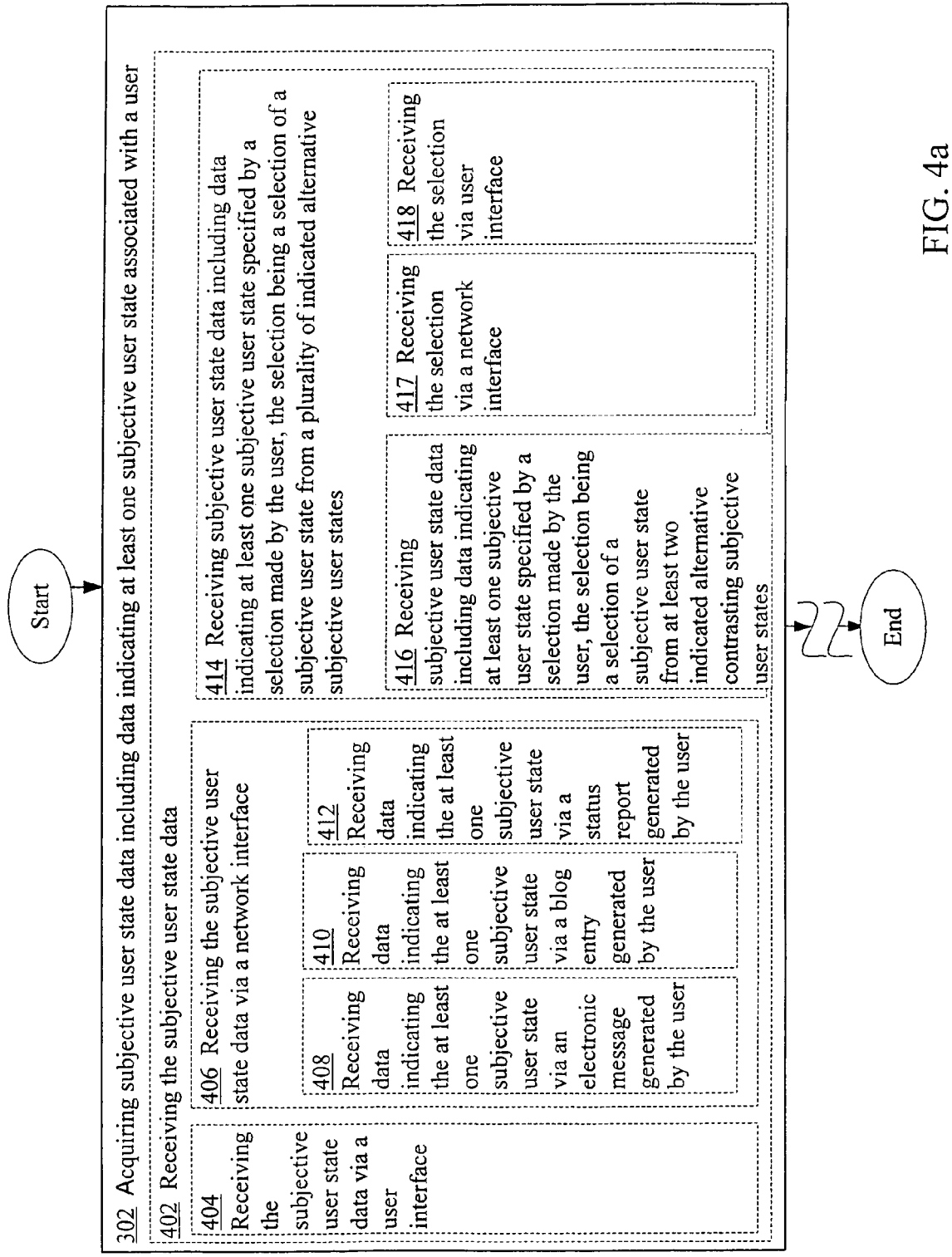
FIG. 4a is a high-level logic flowchart of a process depicting alternate implementations of the subjective user state data acquisition operation 302 of FIG. 3.
Figure 4B:
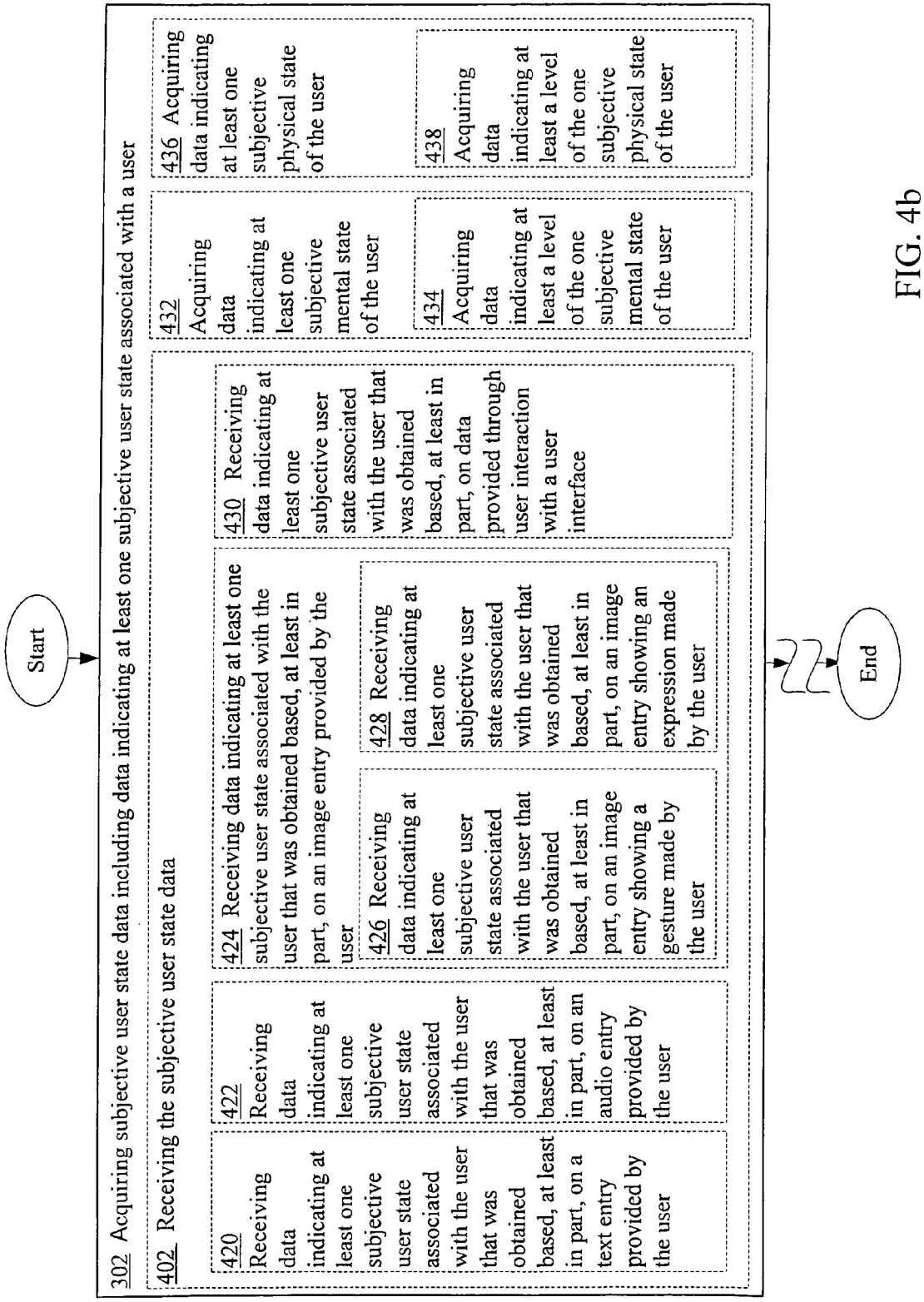
FIG. 4b is a high-level logic flowchart of a process depicting alternate implementations of the subjective user state data acquisition operation 302 of FIG. 3.
Figure 4C:
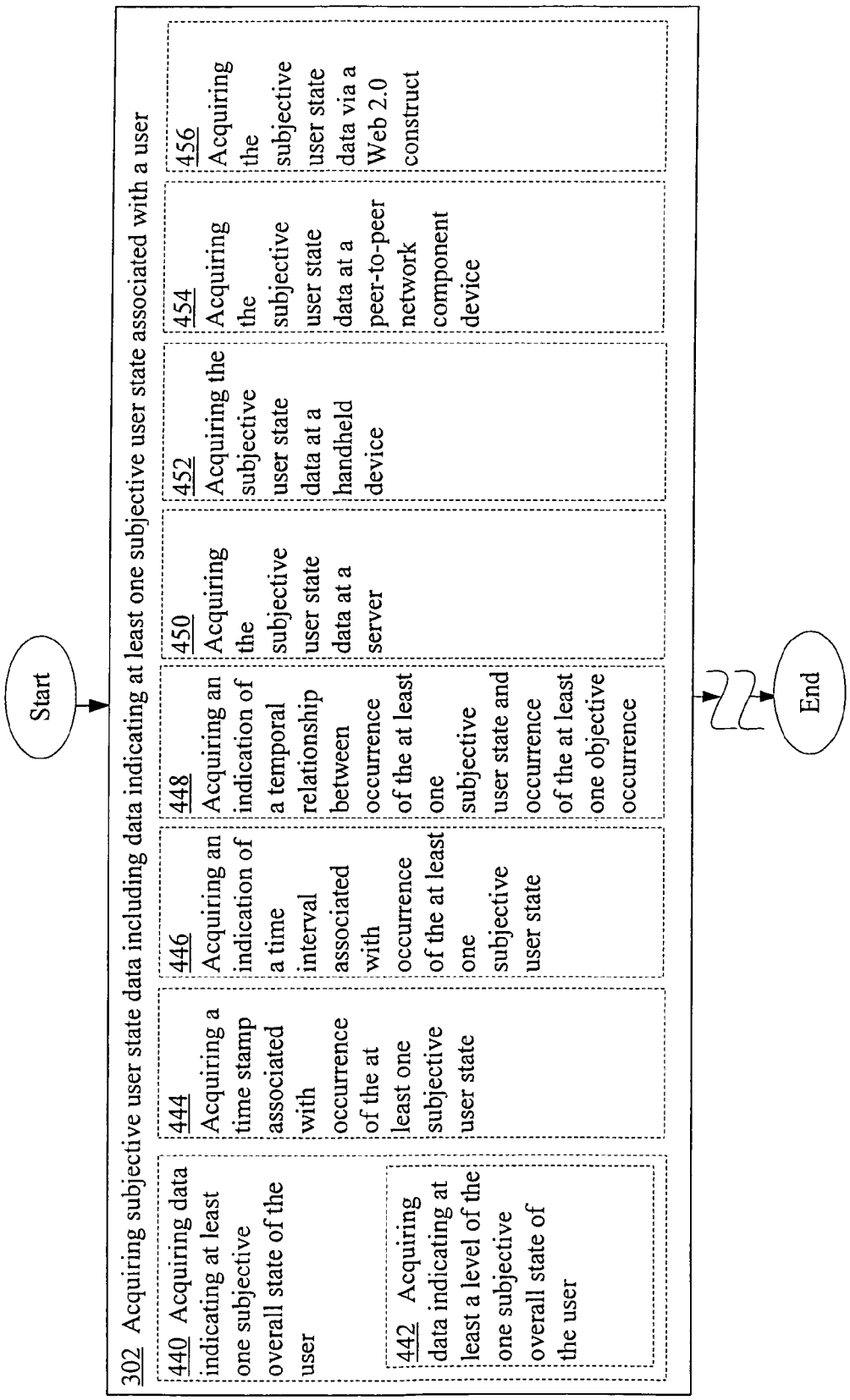
FIG. 4c is a high-level logic flowchart of a process depicting alternate implementations of the subjective user state data acquisition operation 302 of FIG. 3.

In various implementations, the subjective user state data acquisition operation 302 may include one or more additional operations as illustrated in FIGS. 4a, 4b, and 4c. For example, in some implementations the subjective user state data acquisition operation 302 may include a reception operation 402 for receiving the subjective user state data as depicted in FIGS. 4a and 4b. For instance, the subjective user state data reception module 202 (see FIG. 2a) of the computing device 10 receiving (e.g., via network interface 120 or via the user interface 122) the subjective user state data 60.

The reception operation 402 may, in turn, further include one or more additional operations. For example, in some implementations, the reception operation 402 may include an operation 404 for receiving the subjective user state data via a user interface as depicted in FIG. 4a. For instance, the user interface data reception module 204 (see FIG. 2a) of the computing device 10 receiving the subjective user state data 60 via a user interface 122 (e.g., a keypad, a keyboard, a touchscreen, a mouse, an audio system including a microphone, an image capturing system including a video or digital camera, and/or other interface devices).

In some implementations, the reception operation 402 may include an operation 406 for receiving the subjective user state data via a network interface as depicted in FIG. 4a. For instance, the network interface data reception module 206 of the computing device 10 receiving the subjective user state data 60 from a wireless and/or wired network 40 via a network interface 120 (e.g., a NIC).

In various implementations, operation 406 may further include one or more additional operations. For example, in some implementations operation 406 may include an operation 408 for receiving data indicating the at least one subjective user state via an electronic message generated by the user as depicted in FIG. 4a. For instance, the network interface data reception module 206 of the computing device 10 receiving data indicating the at least one subjective user state 60a (e.g., subjective mental state such as feelings of happiness, sadness, anger, frustration, mental fatigue, drowsiness, alertness, and so forth) via an electronic message (e.g., email, IM, or text message) generated by the user 20a.

In some implementations, operation 406 may include an operation 410 for receiving data indicating the at least one subjective user state via a blog entry generated by the user as depicted in FIG. 4a. For instance, the network interface data reception module 206 of the computing device 10 receiving data indicating the at least one subjective user state 60a (e.g., subjective physical state such as physical exhaustion, physical pain such as back pain or toothache, upset stomach, blurry vision, and so forth) via a blog entry such as a microblog entry generated by the user 20a.

In some implementations, operation 406 may include an operation 412 for receiving data indicating the at least one subjective user state via a status report generated by the user as depicted in FIG. 4a. For instance, the network interface data reception module 206 of the computing device 10 receiving data indicating the at least one subjective user state 60a (e.g., subjective overall state of the user 20* such as good, bad, well, exhausted, and so forth) via a status report (e.g., social network site status report) generated by the user 20a.

In some implementations, the reception operation 402 may include an operation 414 for receiving subjective user state data including data indicating at least one subjective user state specified by a selection made by the user, the selection being a selection of a subjective user state from a plurality of indicated alternative subjective user states as depicted in FIG. 4a. For instance, the subjective user state data reception module 202 of the computing device 10 receiving subjective user state data 60 including data indicating at least one subjective user state 60a specified by a selection (e.g., via mobile device 30 or via user interface 122) made by the user 20*, the selection being a selection of a subjective user state from a plurality of indicated alternative subjective user states (e.g., as provided by the mobile device 30 or by the user interface 122). For example, the user 20* may be given the option of selecting one or more subjective user states from a list of identified subjective user states that are shown or indicated by the mobile device 30 or by the user interface 122.

Operation 414 may include one or more additional operations in various alternative implementations. For example, in some implementations, operation 414 may include an operation 416 for receiving subjective user state data including data indicating at least one subjective user state specified by a selection made by the user, the selection being a selection of a subjective user state from at least two indicated alternative contrasting subjective user states as depicted in FIG. 4a. For instance, the subjective user state data reception module 202 of the computing device 10 receiving subjective user state data 60 including data indicating at least one subjective user state 60a specified (e.g., via the mobile device 30 or via the user interface 122) by a selection made by the user 20*, the selection being a selection of a subjective user state from at least two indicated alternative contrasting subjective user states (e.g., is user in pain or not in pain?, or alternatively, is user in extreme pain, user in moderate pain, or user not in pain?).

In some implementations, operation 414 may include an operation 417 for receiving the selection via a network interface as depicted in FIG. 4a. For instance, the network interface data reception module 206 of the computing device 10 receiving the selection of a subjective user state (e.g., a subjective mental state, a subjective physical state, or a subjective overall state) via a network interface 120.

In some implementations, operation 414 may include an operation 418 for receiving the selection via user interface as depicted in FIG. 4a. For instance, the user interface data reception module 204 of the computing device 10 receiving the selection of a subjective user state (e.g., a subjective mental state, a subjective physical state, or a subjective overall state) via a user interface 122.

In some implementations, the reception operation 402 may include an operation 420 for receiving data indicating at least one subjective user state associated with the user that was obtained based, at least in part, on a text entry provided by the user as depicted in FIG. 4b. For instance, the subjective user state data reception module 202 of the computing device 10 receiving data indicating at least one subjective user state 60a (e.g., a subjective mental state, a subjective physical state, or a subjective overall state) associated with the user 20* that was obtained based, at least in part, on a text entry provided by the user 20* (e.g., text data provided by the user 20* via the mobile device 30 or via the user interface 122).

In some implementations, the reception operation 402 may include an operation 422 for receiving data indicating at least one subjective user state associated with the user that was obtained based, at least in part, on an audio entry provided by the user as depicted in FIG. 4b. For instance, the subjective user state data reception module 202 of the computing device 10 receiving data indicating at least one subjective user state 60a (e.g., a subjective mental state, a subjective physical state, or a subjective overall state) associated with the user 20* that was obtained based, at least in part, on an audio entry provided by the user 20* (e.g., audio recording made via the mobile device 30 or via the user interface 122).

In some implementations, the reception operation 402 may include an operation 424 for receiving data indicating at least one subjective user state associated with the user that was obtained based, at least in part, on an image entry provided by the user as depicted in FIG. 4b. For instance, the subjective user state data reception module 202 of the computing device 10 receiving data indicating at least one subjective user state 60a (e.g., a subjective mental state, a subjective physical state, or a subjective overall state) associated with the user 20* that was obtained based, at least in part, on an image entry provided by the user 20* (e.g., one or more images recorded via the mobile device 30 or via the user interface 122).

Operation 424 may further include one or more additional operations in various alternative implementations. For example, in some implementations, operation 424 may include an operation 426 for receiving data indicating at least one subjective user state associated with the user that was obtained based, at least in part, on an image entry showing a gesture made by the user as depicted in FIG. 4b. For instance, the subjective user state data reception module 202 of the computing device 10 receiving data indicating at least one subjective user state 60a (e.g., a subjective user state such as "user is good" or "user is not good") associated with the user 20* that was obtained based, at least in part, on an image entry showing a gesture (e.g., a thumb up or a thumb down) made by the user 20*.

In some implementations, operation 424 may include an operation 428 for receiving data indicating at least one subjective user state associated with the user that was obtained based, at least in part, on an image entry showing an expression made by the user as depicted in FIG. 4b. For instance, the subjective user state data reception module 202 of the computing device 10 receiving data indicating at least one subjective user state 60a (e.g., a subjective mental state such as happiness or sadness) associated with the user 20* that was obtained based, at least in part, on an image entry showing an expression (e.g., a smile or a frown expression) made by the user 20*.

In some implementations, the reception operation 402 may include an operation 430 for receiving data indicating at least one subjective user state associated with the user that was obtained based, at least in part, on data provided through user interaction with a user interface as depicted in FIG. 4b. For instance, the subjective user state data reception module 202 of the computing device 10 receiving data indicating at least one subjective user state 60a associated with the user 20* that was obtained based, at least in part, on data provided through user interaction (e.g., user 20* selecting one subjective user state from a plurality of alternative subjective user states) with a user interface 122 (e.g., keypad, a touchscreen, a microphone, and so forth) of the computing device 10 or with a user interface of the mobile device 30.

In various implementations, the subjective user state data acquisition operation 302 may include an operation 432 for acquiring data indicating at least one subjective mental state of the user as depicted in FIG. 4b. For instance, the subjective user state data acquisition module 102 of the computing device 10 acquiring (e.g., via network interface 120 or via user interface 122) data indicating at least one subjective mental state (e.g., sadness, happiness, alertness or lack of alertness, anger, frustration, envy, hatred, disgust, and so forth) of the user 20*.

In some implementations, operation 432 may further include an operation 434 for acquiring data indicating at least a level of the one subjective mental state of the user as depicted in FIG. 4b. For instance, the subjective user state data acquisition module 102 of the computing device 10 acquiring data indicating at least a level of the one subjective mental state (e.g., extreme sadness or slight sadness) of the user 20*.

In various implementations, the subjective user state data acquisition operation 302 may include an operation 436 for acquiring data indicating at least one subjective physical state of the user as depicted in FIG. 4b. For instance, the subjective user state data acquisition module 102 of the computing device 10 acquiring (e.g., via network interface 120 or via user interface 122) data indicating at least one subjective physical state (e.g., blurry vision, physical pain such as backache or headache, upset stomach, physical exhaustion, and so forth) of the user 20*.

In some implementations, operation 436 may further include an operation 438 for acquiring data indicating at least a level of the one subjective physical state of the user as depicted in FIG. 4b. For instance, the subjective user state data acquisition module 102 of the computing device 10 acquiring data indicating at least a level of the one subjective physical state (e.g., a slight headache or a severe headache) of the user 20*.

In various implementations, the subjective user state data acquisition operation 302 may include an operation 440 for acquiring data indicating at least one subjective overall state of the user as depicted in FIG. 4c. For instance, the subjective user state data acquisition module 102 of the computing device 10 acquiring (e.g., via network interface 120 or via user interface 122) data indicating at least one subjective overall state (e.g., good, bad, wellness, hangover, fatigue, nausea, and so forth) of the user 20*. Note that a subjective overall state, as used herein, may be in reference to any subjective user state that may not fit neatly into the categories of subjective mental state or subjective physical state.

In some implementations, operation 440 may further include an operation 442 for acquiring data indicating at least a level of the one subjective overall state of the user as depicted in FIG. 4c. For instance, the subjective user state data acquisition module 102 of the computing device 10 acquiring data indicating at least a level of the one subjective overall state (e.g., a very bad hangover) of the user 20*.

In some implementations the subjective user state data acquisition operation 302 may include an operation 444 for acquiring a time stamp associated with occurrence of the at least one subjective user state as depicted in FIG. 4c. For instance, the time stamp acquisition module 210 (see FIG. 2a) of the computing device 10 acquiring (e.g., receiving via the network interface 120 or via the user interface 122 as provided by the user 20* or by automatically or self generating) a time stamp (e.g., 10 PM Aug. 4, 2009) associated with occurrence of the at least one subjective user state.

In some implementations the subjective user state data acquisition operation 302 may include an operation 446 for acquiring an indication of a time interval associated with occurrence of the at least one subjective user state as depicted in FIG. 4c. For instance, the time interval acquisition module 212 of the computing device 10 acquiring (e.g., via the network interface 120 or via the user interface 122 as provided by the user 20* or by automatically generating) an indication of a time interval (e.g., 8 AM to 10 AM Jul. 24, 2009) associated with occurrence of the at least one subjective user state.

In some implementations the subjective user state data acquisition operation 302 may include an operation 448 for acquiring an indication of a temporal relationship between occurrence of the at least one subjective user state and occurrence of the at least one objective occurrence as depicted in FIG. 4c. For instance, the temporal relationship acquisition module 214 of the computing device 10 acquiring (e.g., via the network interface 120 or via the user interface 122 as provided by the user 20* or by automatically generating) an indication of a temporal relationship (e.g., before, after, or at least partially concurrently) between occurrence of the at least one subjective user state (e.g., easing of a headache) and occurrence of at least one objective occurrence (e.g., ingestion of aspirin). For example, acquiring an indication that a user's headache eased after taking an aspirin.

In some implementations the subjective user state data acquisition operation 302 may include an operation 450 for acquiring the subjective user state data at a server as depicted in FIG. 4c. For instance, when the computing device 10 is a network server and is acquiring the subjective user state data 60.

In some implementations the subjective user state data acquisition operation 302 may include an operation 452 for acquiring the subjective user state data at a handheld device as depicted in FIG. 4c. For instance, when the computing device 10 is a handheld device such as a mobile phone or a PDA and is acquiring the subjective user state data 60.

In some implementations the subjective user state data acquisition operation 302 may include an operation 454 for acquiring the subjective user state data at a peer-to-peer network component device as depicted in FIG. 4c. For instance, when the computing device 10 is a peer-to-peer network component device and is acquiring the subjective user state data 60.

In some implementations the subjective user state data acquisition operation 302 may include an operation 456 for acquiring the subjective user state data via a Web 2.0 construct as depicted in FIG. 4c. For instance, when the computing device 10 employs a Web 2.0 application in order to acquire the subjective user state data 60.

Figure 5A:
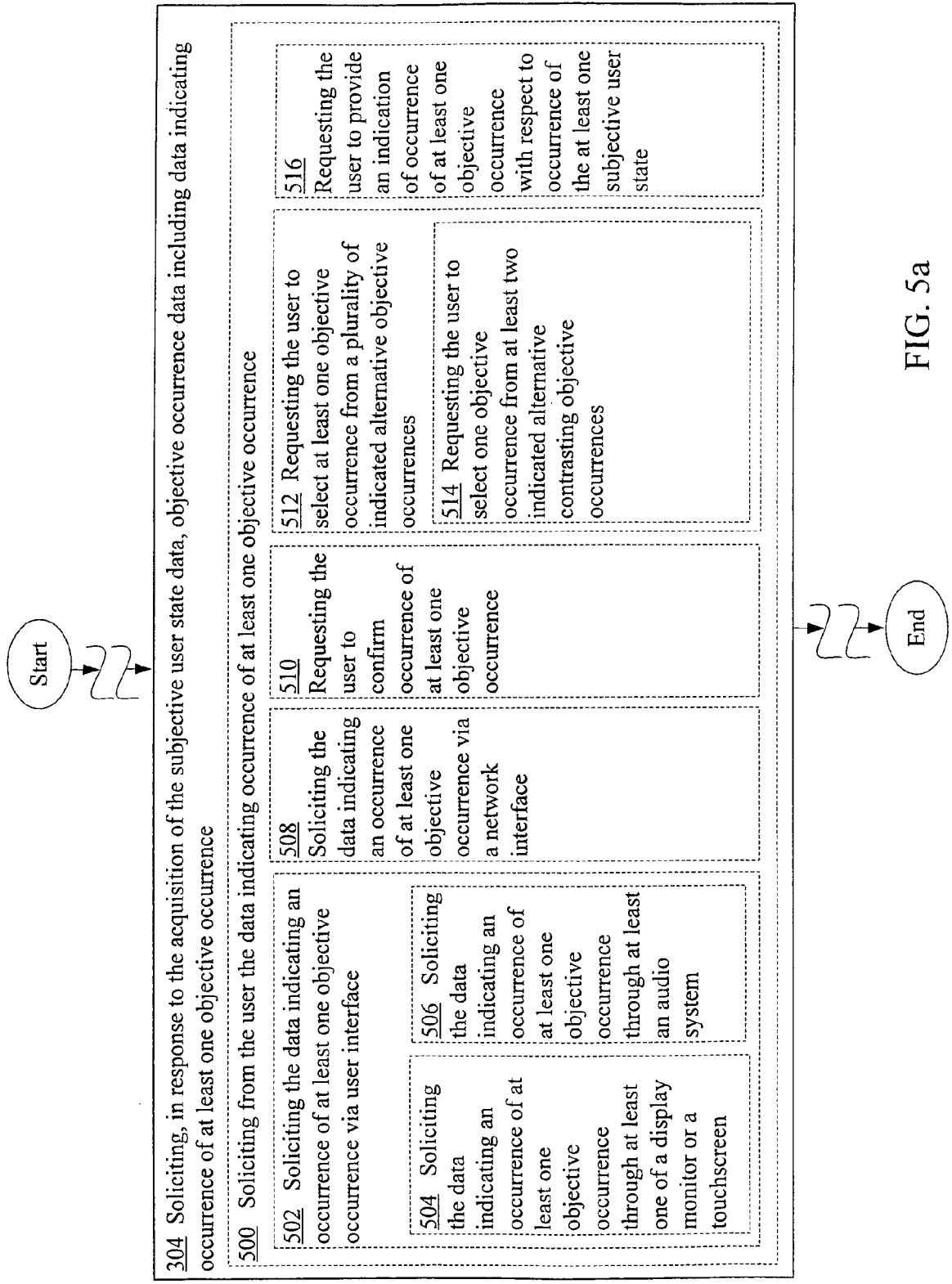
FIG. 5a is a high-level logic flowchart of a process depicting alternate implementations of the objective occurrence data solicitation operation 304 of FIG. 3.
Figure 5B:
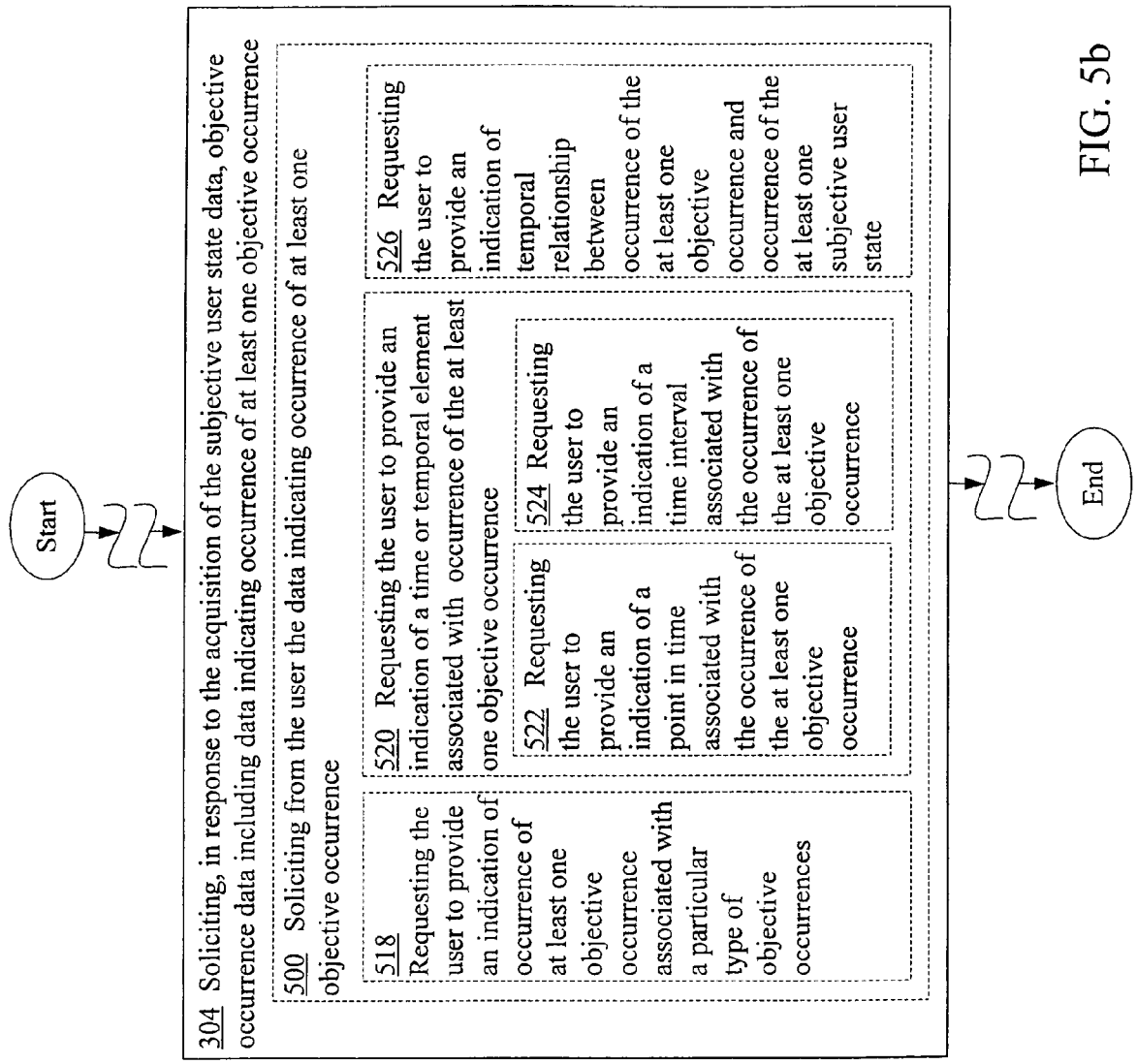
FIG. 5b is a high-level logic flowchart of a process depicting alternate implementations of the objective occurrence data solicitation operation 304 of FIG. 3.

Referring back to FIG. 3, the objective occurrence data solicitation operation 304 in various embodiments may include one or more additional operations as illustrated in FIGS. 5a to 5d. For example, in some implementations, the objective occurrence data solicitation operation 304 may include an operation 500 for soliciting from the user the data indicating occurrence of at least one objective occurrence as depicted in FIGS. 5a and 5b. For instance, the objective occurrence data solicitation module 103 of the computing device 10 soliciting (e.g., via network interface 120 or via user interface 122) from the user 20* the data indicating occurrence of at least one objective occurrence (e.g., ingestion of a food item, medicine, or nutraceutical, exercise or other activities performed by the user 20* or by others, or external events such as weather or performance of the stock market).

Operation 500 may also further include one or more additional operations. For example, in some implementations, operation 500 may include an operation 502 for soliciting the data indicating an occurrence of at least one objective occurrence via user interface as depicted in FIG. 5a. For instance, the user interface solicitation module 216 of the computing device 10 soliciting (e.g., requesting or seeking from the user 20b) the data indicating an occurrence of at least one objective occurrence (e.g., ingestion of a food item, a medicine, or a nutraceutical by the user 20b) via user interface 122.

Operation 502, in turn, may include one or more additional operations. For example, in some implementations, operation 502 may include an operation 504 for soliciting the data indicating an occurrence of at least one objective occurrence through at least one of a display monitor or a touchscreen as depicted in FIG. 5a. For instance, the user interface solicitation module 216 of the computing device 10 soliciting (e.g., requesting or seeking from the user 20b) the data indicating an occurrence of at least one objective occurrence (e.g., social, work, or exercise activity performed by the user 20b or by a third party 50) through at least one of a display monitor or a touchscreen.

In some implementations, operation 502 may include an operation 506 for soliciting the data indicating an occurrence of at least one objective occurrence through at least an audio system as depicted in FIG. 5a. For instance, the user interface solicitation module 216 of the computing device 10 soliciting the data indicating an occurrence of at least one objective occurrence (e.g., activity performed by a third party 50 or a physical characteristic of the user 20b such as blood pressure) through at least an audio system (e.g., a speaker system).

In various implementations, operation 500 may include an operation 508 for soliciting the data indicating an occurrence of at least one objective occurrence via a network interface as depicted in FIG. 5a. For instance, the network interface solicitation module 215 (see FIG. 2b) soliciting (e.g., requesting or seeking from the user 20a, one or more third parties 50, or from one or more sensors 35) the data indicating an occurrence of at least one objective occurrence (e.g., an external event such as local weather or the location of the user 20*) via a network interface 120.

In some implementations, operation 500 may include an operation 510 for requesting the user to confirm occurrence of at least one objective occurrence as depicted in FIG. 5a. For instance, the requesting module 217 (see FIG. 2b) of the computing device 10 requesting (e.g., transmitting a request or an inquiry via the network interface 120 or displaying a request or an inquiry via the user interface 122) the user 20* to confirm occurrence of at least one objective occurrence (e.g., did user 20* ingest a particular type of medicine?).

In some implementations, operation 500 may include an operation 512 for requesting the user to select at least one objective occurrence from a plurality of indicated alternative objective occurrences as depicted in FIG. 5a. For instance, the requesting module 217 of the computing device 10 requesting (e.g., transmitting a request via the network interface 120 or displaying a request via the user interface 122) the user 20* to select at least one objective occurrence from a plurality of indicated alternative objective occurrences (e.g., did user ingest aspirin, ibuprofen, or acetaminophen today?). For example, the user 20* may be given the option of selecting one or more objective occurrences from a list of identified objective occurrences that are shown or indicated by the mobile device 30 or by the user interface 122.

Operation 512, in various implementations, may in turn include an operation 514 for requesting the user to select one objective occurrence from at least two indicated alternative contrasting objective occurrences as depicted in FIG. 5a. For instance, the requesting module 217 of the computing device 10 requesting (e.g., transmitting a request via the network interface 120 or displaying a request via the user interface 122) the user 20* to select one objective occurrence from at least two indicated alternative contrasting objective occurrences (e.g., ambient temperature being greater than or equal to 90 degrees or less than 90 degrees?).

In some implementations, operation 500 may include an operation 516 for requesting the user to provide an indication of occurrence of at least one objective occurrence with respect to occurrence of the at least one subjective user state as depicted in FIG. 5a. For instance, the requesting module 217 of the computing device 10 requesting (e.g., via the network interface 120 or via the user interface 122) the user 20* to provide an indication of occurrence of at least one objective occurrence with respect to occurrence of the at least one subjective user state (you felt sick this morning, did you drink last night?).

In some implementations, operation 500 may include an operation 518 for requesting the user to provide an indication of occurrence of at least one objective occurrence associated with a particular type of objective occurrences as depicted in FIG. 5b. For instance, the requesting module 217 of the computing device 10 requesting (e.g., via the network interface 120 or via the user interface 122) the user 20* to provide an indication of occurrence of at least one objective occurrence associated with a particular type of objective occurrences (e.g., what type of exercise did you do today?)

In some implementations, operation 500 may include an operation 520 for requesting the user to provide an indication of a time or temporal element associated with occurrence of the at least one objective occurrence as depicted in FIG. 5*b*. For instance, the requesting module 217 of the computing device 10 requesting (e.g., via the network interface 120 or via the user interface 122) the user 20* to provide an indication of a time or temporal element associated with occurrence of the at least one objective occurrence (e.g., what time did you exercise or did you exercise before or after eating lunch?).

Operation 520 in various implementations may further include one or more additional operations. For example, in some implementations, operation 520 may include an operation 522 for requesting the user to provide an indication of a point in time associated with the occurrence of the at least one objective occurrence as depicted in FIG. 5*b*. For instance, the requesting module 217 of the computing device 10 requesting (e.g., via the network interface 120 or via the user interface 122) the user 20* to provide an indication of a point in time associated with the occurrence of the at least one objective occurrence (e.g., at what time of the day did you ingest the aspirin?)

In some implementations, operation 520 may include an operation 524 for requesting the user to provide an indication of a time interval associated with the occurrence of the at least one objective occurrence as depicted in FIG. 5*b*. For instance, the requesting module 217 of the computing device 10 requesting (e.g., via the network interface 120 or via the user interface 122) the user 20* to provide an indication of a time interval associated with the occurrence of the at least one objective occurrence (e.g., from what time to what time did you take your walk?).

In some implementations, operation 500 may include an operation 526 for requesting the user to provide an indication of temporal relationship between occurrence of the at least one objective occurrence and occurrence of the at least one subjective user state as depicted in FIG. 5*b*. For instance, the requesting module 217 of the computing device 10 requesting (e.g., via the network interface 120 or via the user interface 122) the user 20* to provide an indication of temporal relationship between occurrence of the at least one objective occurrence and occurrence of the at least one subjective user state (e.g., did you ingest the ibuprofen before or after your headache went away?).

Figure 5C:
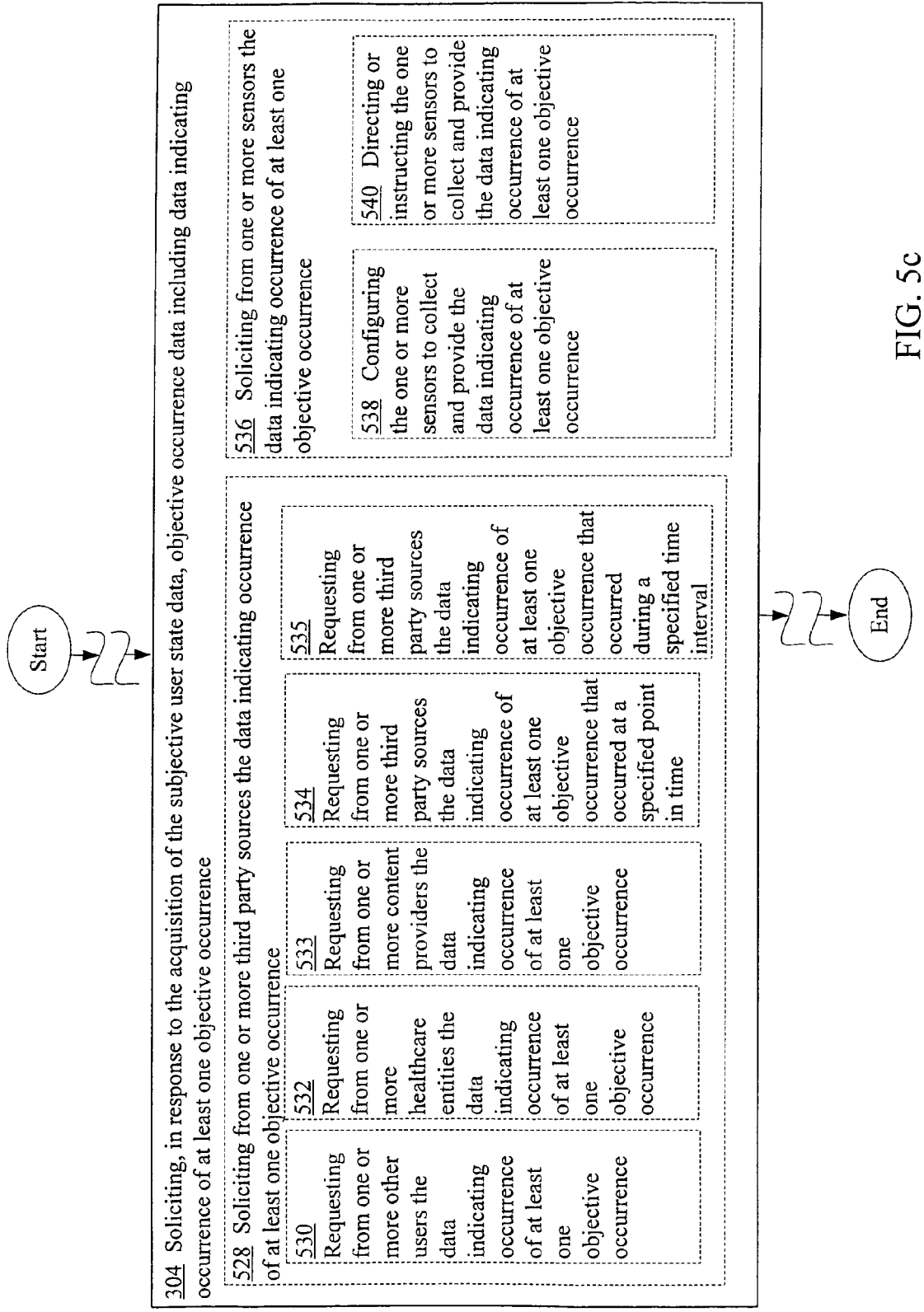
FIG. 5c is a high-level logic flowchart of a process depicting alternate implementations of the objective occurrence data solicitation operation 304 of FIG. 3.

In various implementations, the solicitation operation 304 of FIG. 3 may include an operation 528 for soliciting from one or more third party sources the data indicating occurrence of at least one objective occurrence as depicted in FIG. 5*c*. For instance, the objective occurrence data solicitation module 103 of the computing device 10 soliciting from one or more third party sources (e.g., a fitness gym, a healthcare facility, another user, a content provider, or other third party source) the data indicating occurrence of at least one objective occurrence (e.g., weather, medical treatment, user 20* or third party activity, and so forth).

Operation 528 may, in turn, include one or more additional operations in various alternative implementations. For example, in some implementations, operation 528 may include an operation 530 for requesting from one or more other users the data indicating occurrence of at least one objective occurrence as depicted in FIG. 5*c*. For instance, the requesting module 217 of the computing device 10 requesting (e.g., via wireless and/or wired network 40) from one or more other users (e.g., other microbloggers) the data indicating occurrence of at least one objective occurrence (e.g., user activities observed by the one or more other users or the one or more other users' activities).

In some implementations, operation 528 may include an operation 532 for requesting from one or more healthcare entities the data indicating occurrence of at least one objective occurrence as depicted in FIG. 5*c*. For instance, the requesting module 217 of the computing device 10 requesting (e.g., via an electronic message) from one or more healthcare entities (e.g., physician's or dental office, medical clinic, hospital, and so forth) the data indicating occurrence of at least one objective occurrence (e.g., occurrence of a medical or dental treatment).

In some implementations, operation 528 may include an operation 533 for requesting from one or more content providers the data indicating occurrence of at least one objective occurrence as depicted in FIG. 5*c*. For instance, the requesting module 217 of the computing device 10 requesting (e.g., via a network interface 120) from one or more content providers the data indicating occurrence of at least one objective occurrence (e.g., weather or stock market performance).

In some implementations, operation 528 may include an operation 534 for requesting from one or more third party sources the data indicating occurrence of at least one objective occurrence that occurred at a specified point in time as depicted in FIG. 5*c*. For instance, the requesting module 217 of the computing device 10 requesting (e.g., via a network interface 120) from one or more third party sources (e.g., dental office) the data indicating occurrence of at least one objective occurrence that occurred at a specified point in time (e.g., asking whether the user 20* was sedated with nitrous oxide at 3 PM during a dental procedure).

In some implementations, operation 528 may include an operation 535 for requesting from one or more third party sources the data indicating occurrence of at least one objective occurrence that occurred during a specified time interval as depicted in FIG. 5*c*. For instance, the requesting module 217 of the computing device 10 requesting (e.g., via a network interface 120) from one or more third party sources (e.g., fitness instructor or gym) the data indicating occurrence of at least one objective occurrence that occurred during a specified time interval (e.g., did user exercise on the treadmill between 6 AM and 12 PM?).

In some implementations, the solicitation operation 304 of FIG. 3 may include an operation 536 for soliciting from one or more sensors the data indicating occurrence of at least one objective occurrence as depicted in FIG. 5*c*. For instance, the objective occurrence data solicitation module 103 of the computing device 10 soliciting (e.g., via a network interface 120) from one or more sensors 35 (e.g., GPS) the data indicating occurrence of at least one objective occurrence (e.g., user location).

Operation 536 may include, in various implementations, one or more additional operations. For example, in some implementations, operation 536 may include an operation 538 for configuring the one or more sensors to collect and provide the data indicating occurrence of at least one objective occurrence as depicted in FIG. 5*c*. For instance, the configuration module 218 of the computing device 10 configuring the one or more sensors 35 (e.g., blood pressure device, glucometer, GPS, pedometer, or other sensors 35) to collect and provide the data indicating occurrence of at least one objective occurrence.

In some implementations, operation 536 may include an operation 540 for directing or instructing the one or more sensors to collect and provide the data indicating occurrence of at least one objective occurrence as depicted in FIG. 5c. For instance, the directing/instructing module 219 of the computing device directing or instructing the one or more sensors 35 (e.g., blood pressure device, glucometer, GPS, pedometer, or other sensors 35) to collect and provide the data indicating occurrence of at least one objective occurrence.

Figure 5D:
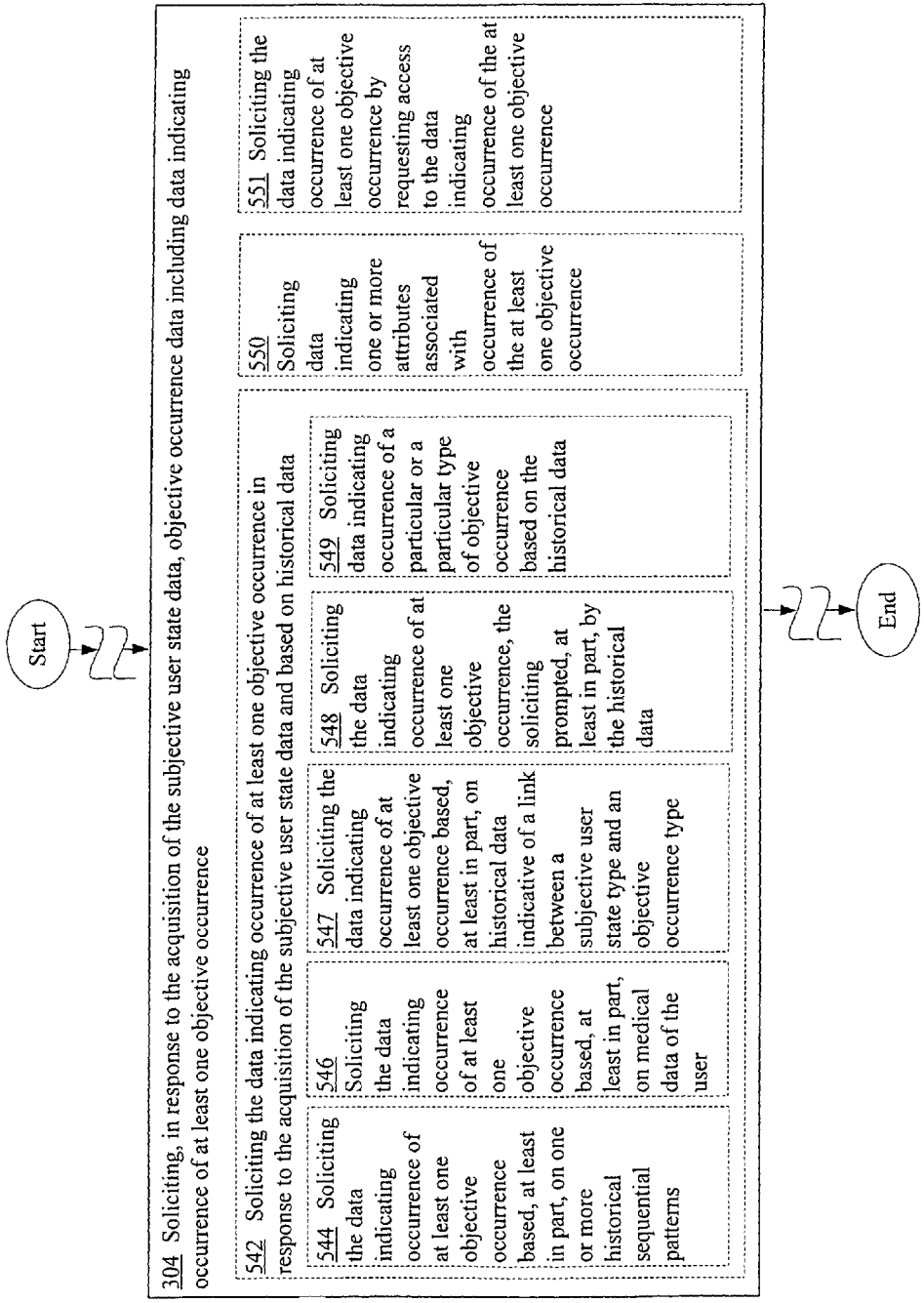
FIG. 5d is a high-level logic flowchart of a process depicting alternate implementations of the objective occurrence data solicitation operation 304 of FIG. 3.

The solicitation operation 304 of FIG. 3, in various implementations, may include an operation 542 for soliciting the data indicating occurrence of at least one objective occurrence in response to the acquisition of the subjective user state data and based on historical data as depicted in FIG. 5d. For instance, the objective occurrence data solicitation module 103 of the computing device 10 being prompted to soliciting the data indicating occurrence of at least one objective occurrence (e.g., asking whether the user 20* ate anything or ate a chocolate sundae) in response to the acquisition of the subjective user state data 60 (e.g., subjective user state data 60 indicating a stomach ache) and based on historical data 72 (e.g., a previously determined sequential pattern associated with the user 20* indicating that the user 20* may have gotten a stomach ache after eating a chocolate sundae).

In various implementations, operation 542 may further include one or more additional operations. For example, in some implementations, operation 542 may include an operation 544 for soliciting the data indicating occurrence of at least one objective occurrence based, at least in part, on one or more historical sequential patterns as depicted in FIG. 5d. For instance, the objective occurrence data solicitation module 103 of the computing device 10 soliciting (e.g., via network interface 120 or via user interface 122) the data indicating occurrence of at least one objective occurrence based, at least in part, on referencing of one or more historical sequential patterns (e.g., historical sequential patterns derived from general population or from a group of users 20*).

In some implementations, operation 542 may include an operation 546 for soliciting the data indicating occurrence of at least one objective occurrence based, at least in part, on medical data of the user as depicted in FIG. 5d. For instance, the objective occurrence data solicitation module 103 of the computing device 10 soliciting (e.g., via network interface 120 or via user interface 122) the data indicating occurrence of at least one objective occurrence based, at least in part, on medical data of the user 20* (e.g., genetic, metabolome, or proteome data of the user).

In some implementations, operation 542 may include an operation 547 for soliciting the data indicating occurrence of at least one objective occurrence based, at least in part, on historical data indicative of a link between a subjective user state type and an objective occurrence type as depicted in FIG. 5d. For instance, the objective occurrence data solicitation module 103 of the computing device 10 soliciting (e.g., via network interface 120 or via user interface 122) the data indicating occurrence of at least one objective occurrence (e.g., local weather) based, at least in part, on historical data 72 indicative of a link between a subjective user state type and an objective occurrence type (e.g., link between moods of people and weather).

In some implementations, operation 542 may include an operation 548 for soliciting the data indicating occurrence of at least one objective occurrence, the soliciting prompted, at least in part, by the historical data as depicted in FIG. 5d. For instance, the objective occurrence data solicitation module 103 of the computing device 10 soliciting (e.g., via network interface 120 or via user interface 122) the data indicating occurrence of at least one objective occurrence (e.g., weather), the soliciting prompted, at least in part, by the historical data 72 (e.g., historical data 72 that indicates that the user 20* or people in the general population tend to be gloomy (a subjective user state) when the weather is overcast).

In some implementations, operation 542 may include an operation 549 for soliciting data indicating occurrence of a particular or a particular type of objective occurrence based on the historical data as depicted in FIG. 5d. For instance, the objective occurrence data solicitation module 103 of the computing device 10 soliciting (e.g., via network interface 120 or via user interface 122) data indicating occurrence of a particular or a particular type of objective occurrence (e.g., requesting performance of shares of particular stock) based on the historical data 72 (e.g., historical data 72 that indicates that the user 20* is happy when the shares of particular stocks rise).

In some implementations, the solicitation operation 304 of FIG. 3 may include an operation 550 for soliciting data indicating one or more attributes associated with occurrence of the at least one objective occurrence as depicted in FIG. 5d. For instance, the objective occurrence data solicitation module 103 of the computing device 10 soliciting (e.g., via network interface 120 or via user interface 122) data indicating one or more attributes associated with occurrence of the at least one objective occurrence (e.g., how hard or how long did it rain on Tuesday?).

In some implementations, the solicitation operation 304 may include an operation 551 for soliciting the data indicating occurrence of at least one objective occurrence by requesting access to the data indicating occurrence of the at least one objective occurrence as depicted in FIG. 5d. For instance, the objective occurrence data solicitation module 103 of the computing device 10 soliciting (e.g., via network interface 120) the data indicating occurrence of at least one objective occurrence by requesting access to the data indicating occurrence of the at least one objective occurrence (e.g., by requesting access to the file containing the data or to the location of the data or to the data itself).

Figure 6A:
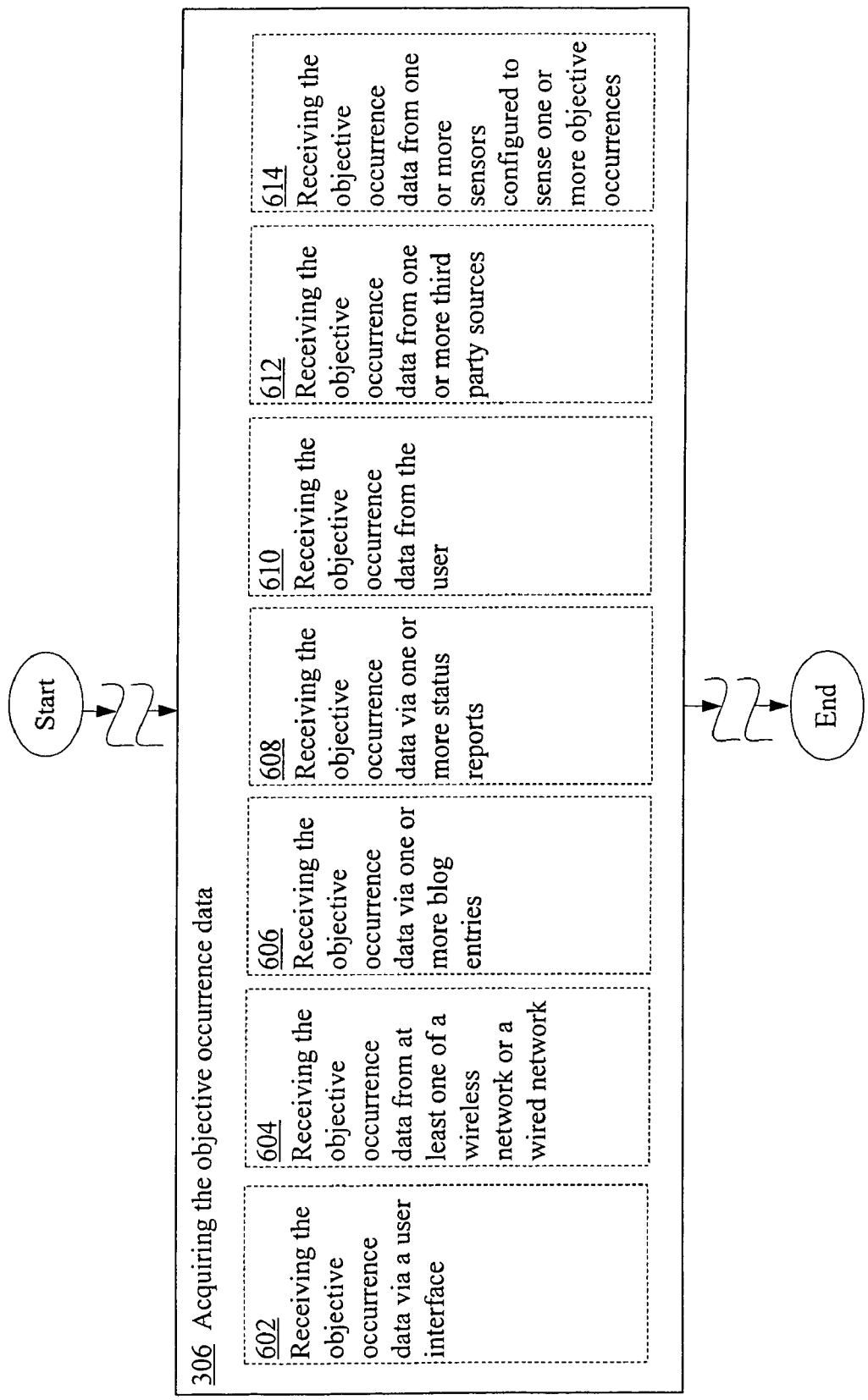
FIG. 6a is a high-level logic flowchart of a process depicting alternate implementations of the objective occurrence data acquisition operation 306 of FIG. 3.
Figure 6B:
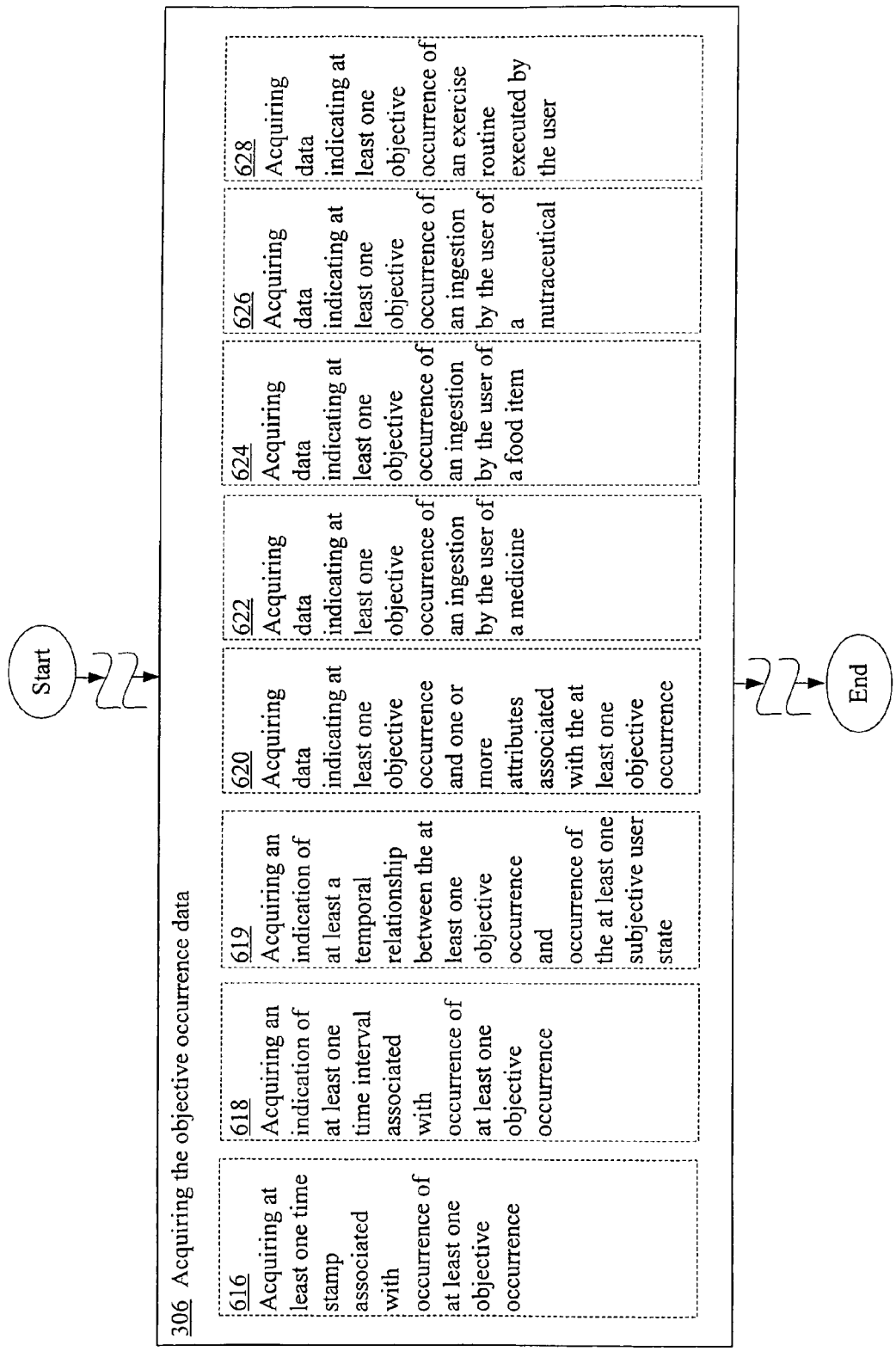
FIG. 6b is a high-level logic flowchart of a process depicting alternate implementations of the objective occurrence data acquisition operation 306 of FIG. 3.
Figure 6C:
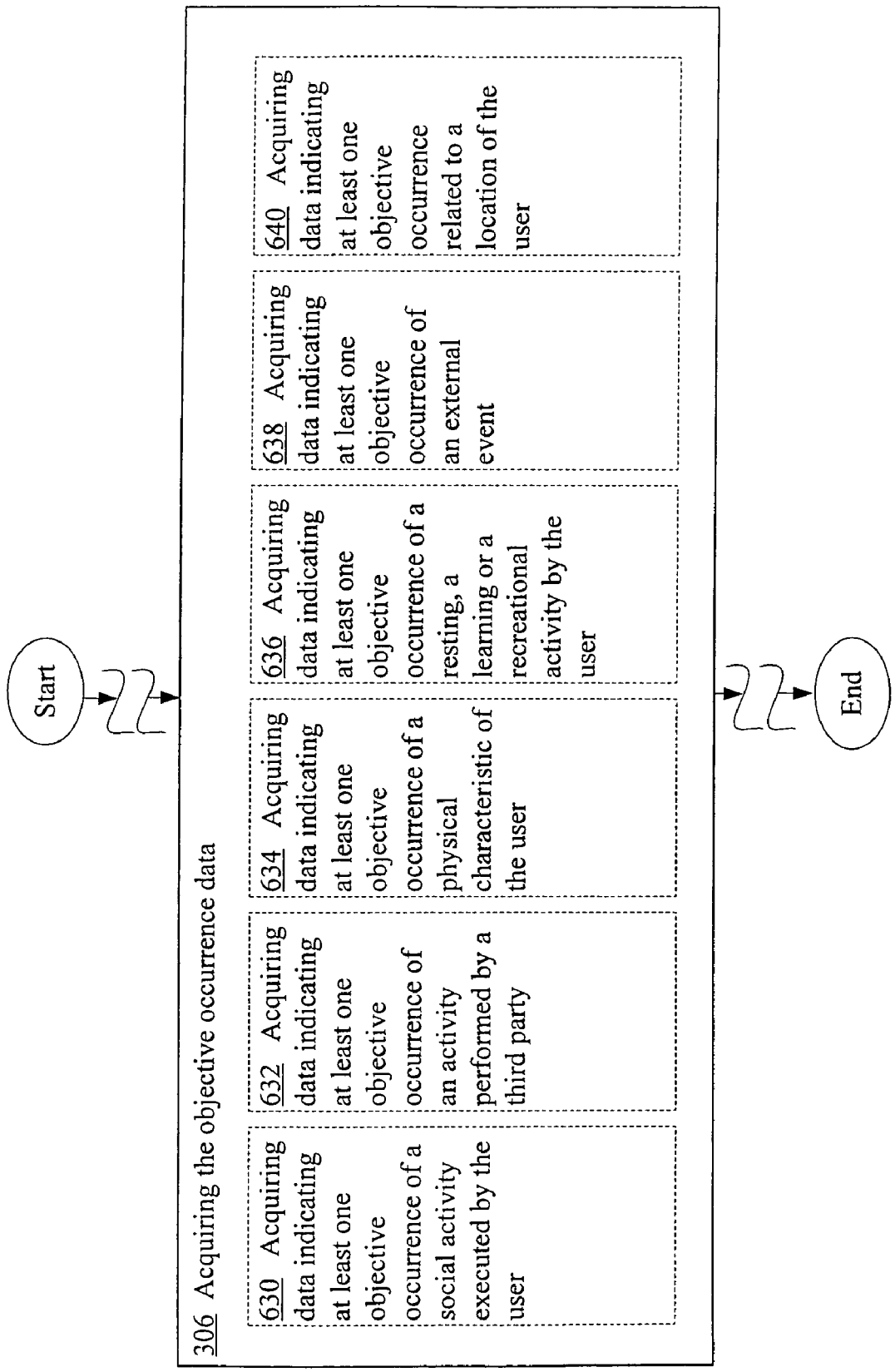
FIG. 6c is a high-level logic flowchart of a process depicting alternate implementations of the objective occurrence data acquisition operation 306 of FIG. 3.

In various embodiments, the objective occurrence data acquisition operation 306 of FIG. 3 may include one or more additional operations as illustrated in FIGS. 6a to 6c. For example, in some implementations, the objective occurrence data acquisition operation 306 may include an operation 602 for receiving the objective occurrence data via a user interface as depicted in FIG. 6a. For instance, the objective occurrence data user interface reception module 226 (see FIG. 2c) of the computing device 10 receiving the objective occurrence data 70* via a user interface 122 (e.g., a key pad, a touchscreen, an audio system including a microphone, an image capturing system such as a digital or video camera, or other user interfaces 122).

In some implementations, the objective occurrence data acquisition operation 306 may include an operation 604 for receiving the objective occurrence data from at least one of a wireless network or a wired network as depicted in FIG. 6a. For instance, the objective occurrence data network interface reception module 227 of the computing device 10 receiving (e.g., via the network interface 120) the objective occurrence data 70* from at least one of a wireless and/or a wired network 40.

In some implementations, the objective occurrence data acquisition operation 306 may include an operation 606 for receiving the objective occurrence data via one or more blog entries as depicted in FIG. 6a. For instance, the reception module 224 of the computing device 10 receiving (e.g., via network interface 120) the objective occurrence data 70*a* or 70*c* via one or more blog entries (e.g., microblog entries).

In some implementations, the objective occurrence data acquisition operation 306 may include an operation 608 for receiving the objective occurrence data via one or more status reports as depicted in FIG. 6*a*. For instance, the reception module 224 of the computing device 10 receiving (e.g., via network interface 120) the objective occurrence data 70* via one or more status reports (e.g., as generated by the user 20*** or by one or more third parties 50**).

In some implementations, the objective occurrence data acquisition operation 306 may include an operation 610 for receiving the objective occurrence data from the user as depicted in FIG. 6*a*. For instance, the reception module 224 of the computing device 10 receiving (e.g., via network interface 120 or via the user interface 122) the objective occurrence data 70* from the user 20***.

In some implementations, the objective occurrence data acquisition operation 306 may include an operation 612 for receiving the objective occurrence data from one or more third party sources as depicted in FIG. 6*a*. For instance, the reception module 224 of the computing device 10 receiving (e.g., via network interface 120) the objective occurrence data 70* from one or more third party sources (e.g., other users 20***, healthcare entities, content providers, or other third party sources).

In some implementations, the objective occurrence data acquisition operation 306 may include an operation 614 for receiving the objective occurrence data from one or more sensors configured to sense one or more objective occurrences as depicted in FIG. 6*a*. For instance, the reception module 224 of the computing device 10 receiving (e.g., via network interface 120) the objective occurrence data 70* from one or more sensors 35** (e.g., a physiological sensing device, a physical activity sensing device such as a pedometer, a GPS, and so forth) configured to sense one or more objective occurrences.

In some implementations, the objective occurrence data acquisition operation 306 may include an operation 616 for acquiring at least one time stamp associated with occurrence of at least one objective occurrence as depicted in FIG. 6*b*. For instance, the time stamp acquisition module 230 (see FIG. 2*c*) of the computing device 10 acquiring (e.g., via the network interface 120, via the user interface 122 as provided by the user 20*, or by automatically generating) at least one time stamp associated with occurrence of at least one objective occurrence.

In some implementations, the objective occurrence data acquisition operation 306 may include an operation 618 for acquiring an indication of at least one time interval associated with occurrence of at least one objective occurrence as depicted in FIG. 6*b*. For instance, the time interval acquisition module 231 of the computing device 10 acquiring (e.g., via the network interface 120, via the user interface 122 as provided by the user 20*, or by automatically generating) an indication of at least one time interval associated with occurrence of at least one objective occurrence.

In some implementations, the objective occurrence data acquisition operation 306 may include an operation 619 for acquiring an indication of at least a temporal relationship between the at least one objective occurrence and occurrence of the at least one subjective user state as depicted in FIG. 6*b*. For instance, the temporal relationship acquisition module 232 of the computing device 10 acquiring (e.g., via the network interface 120, via the user interface 122 as provided by the user 20*, or by automatically generating) an indication of at least a temporal relationship (e.g., before, after, or at least partially concurrently) between the at least one objective occurrence and occurrence of the at least one subjective user state.

In some implementations, the objective occurrence data acquisition operation 306 may include an operation 620 for acquiring data indicating at least one objective occurrence and one or more attributes associated with the at least one objective occurrence as depicted in FIG. 6*b*. For instance, the objective occurrence data acquisition module 104 of the computing device 10 acquiring data indicating at least one objective occurrence (e.g., ingestion of a medicine or food item) and one or more attributes (e.g., quality, quantity, brand, and/or source of the medicine or food item ingested) associated with the at least one objective occurrence.

In some implementations, the objective occurrence data acquisition operation 306 may include an operation 622 for acquiring data indicating at least one objective occurrence of an ingestion by the user of a medicine as depicted in FIG. 6*b*. For instance, the objective occurrence data acquisition module 104 of the computing device 10 acquiring (e.g., via the network interface 120 or via the user interface 122) data indicating at least one objective occurrence of an ingestion by the user 20* of a medicine (e.g., a dosage of a beta blocker).

In some implementations, the objective occurrence data acquisition operation 306 may include an operation 624 for acquiring data indicating at least one objective occurrence of an ingestion by the user of a food item as depicted in FIG. 6*b*. For instance, the objective occurrence data acquisition module 104 of the computing device 10 acquiring (e.g., via the network interface 120 or via the user interface 122) data indicating at least one objective occurrence of an ingestion by the user 20* of a food item (e.g., an orange).

In some implementations, the objective occurrence data acquisition operation 306 may include an operation 626 for acquiring data indicating at least one objective occurrence of an ingestion by the user of a nutraceutical as depicted in FIG. 6*b*. For instance, the objective occurrence data acquisition module 104 of the computing device 10 acquiring (e.g., via the network interface 120 or via the user interface 122) data indicating at least one objective occurrence of an ingestion by the user 20* of a nutraceutical (e.g. broccoli).

In some implementations, the objective occurrence data acquisition operation 306 may include an operation 628 for acquiring data indicating at least one objective occurrence of an exercise routine executed by the user as depicted in FIG. 6*b*. For instance, the objective occurrence data acquisition module 104 of the computing device 10 acquiring (e.g., via the network interface 120 or via the user interface 122) data indicating at least one objective occurrence of an exercise routine (e.g., working out on a exercise machine such as a treadmill) executed by the user 20*.

In some implementations, the objective occurrence data acquisition operation 306 may include an operation 630 for acquiring data indicating at least one objective occurrence of a social activity executed by the user as depicted in FIG. 6*c*. For instance, the objective occurrence data acquisition module 104 of the computing device 10 acquiring (e.g., via the network interface 120 or via the user interface 122) data indicating at least one objective occurrence of a social activity (e.g., hiking with friends) executed by the user 20*.

In some implementations, the objective occurrence data acquisition operation 306 may include an operation 632 for acquiring data indicating at least one objective occurrence of an activity performed by a third party as depicted in FIG. 6*c*. For instance, the objective occurrence data acquisition module 104 of the computing device 10 acquiring (e.g., via the network interface 120 or via the user interface 122) data indicating at least one objective occurrence of an activity (e.g., boss on a vacation) performed by a third party 50.

In some implementations, the objective occurrence data acquisition operation 306 may include an operation 634 for acquiring data indicating at least one objective occurrence of a physical characteristic of the user as depicted in FIG. 6*c*. For instance, the objective occurrence data acquisition module 104 of the computing device 10 acquiring (e.g., via the network interface 120 or via the user interface 122) data indicating at least one objective occurrence of a physical characteristic (e.g., a blood sugar level) of the user 20*. Note that a physical characteristic such as a blood sugar level could be determined using a device such as a glucometer and then reported by the user 20*, by a third party 50, or by the device (e.g., glucometer) itself.

In some implementations, the objective occurrence data acquisition operation 306 may include an operation 636 for acquiring data indicating at least one objective occurrence of a resting, a learning or a recreational activity by the user as depicted in FIG. 6*c*. For instance, the objective occurrence data acquisition module 104 of the computing device 10 acquiring (e.g., via the network interface 120 or via the user interface 122) data indicating at least one objective occurrence of a resting (e.g., sleeping), a learning (e.g., reading), or a recreational activity (e.g., a round of golf) by the user 20*.

In some implementations, the objective occurrence data acquisition operation 306 may include an operation 638 for acquiring data indicating at least one objective occurrence of an external event as depicted in FIG. 6*c*. For instance, the objective occurrence data acquisition module 104 of the computing device 10 acquiring (e.g., via the network interface 120 or via the user interface 122) data indicating at least one objective occurrence of an external event (e.g., rain storm).

In some implementations, the objective occurrence data acquisition operation 306 may include an operation 640 for acquiring data indicating at least one objective occurrence related to a location of the user as depicted in FIG. 6*c*. For instance, the objective occurrence data acquisition module 104 of the computing device 10 acquiring (e.g., via the network interface 120 or via the user interface 122) data indicating at least one objective occurrence related to a location (e.g., work office at a first point or interval in time) of the user 20*. In some instances, such data may be provided by the user 20* via the user interface 122 (e.g., in the case where the computing device 10 is a local device) or via the mobile device 30 (e.g., in the case where the computing device 10 is a network server). Alternatively, such data may be provided directly by a sensor device 35 such as a GPS device, or by a third party 50.

Figure 7A:
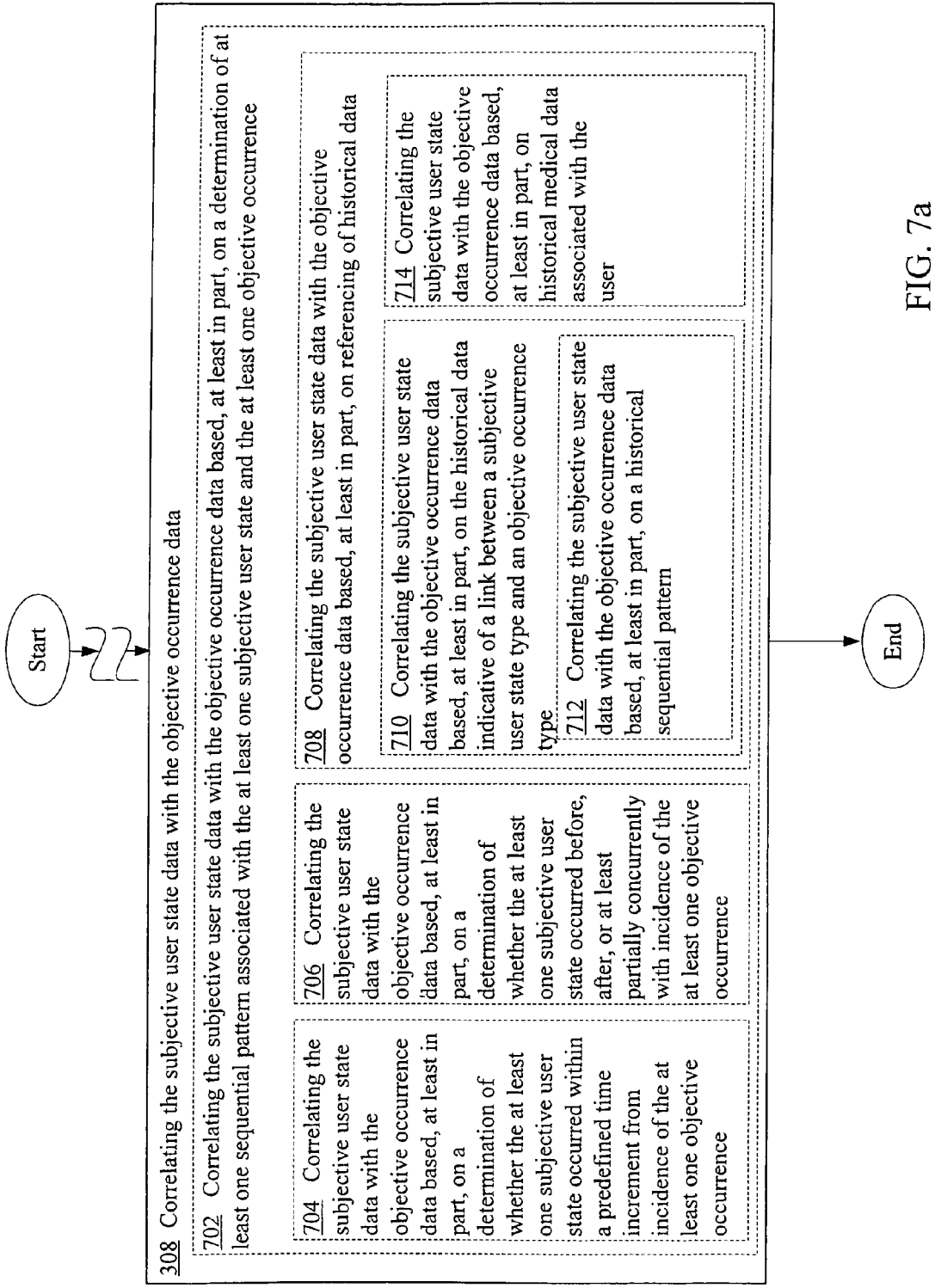
FIG. 7a is a high-level logic flowchart of a process depicting alternate implementations of the correlation operation 308 of FIG. 3.

Referring back to FIG. 3, the correlation operation 308 may include one or more additional operations in various alternative implementations. For example, in various implementations, the correlation operation 308 may include an operation 702 for correlating the subjective user state data with the objective occurrence data based, at least in part, on a determination of at least one sequential pattern associated with the at least one subjective user state and the at least one objective occurrence as depicted in FIG. 7*a*. For instance, the correlation module 106 of the computing device 10 correlating the subjective user state data 60 with the objective occurrence data 70* based, at least in part, on a determination (e.g., as made by the sequential pattern determination module 236) of at least one sequential pattern associated with the at least one subjective user state and the at least one objective occurrence.

In various alternative implementations, operation 702 may include one or more additional operations. For example, in some implementations, operation 702 may include an operation 704 for correlating the subjective user state data with the objective occurrence data based, at least in part, on a determination of whether the at least one subjective user state occurred within a predefined time increment from incidence of the at least one objective occurrence as depicted in FIG. 7*a*. For instance, the correlation module 106 of the computing device 10 correlating the subjective user state data 60 with the objective occurrence data 70* based, at least in part, on a determination by the "within predefined time increment determination" module 238 (see FIG. 2*d*) of whether the at least one subjective user state occurred within a predefined time increment from incidence of the at least one objective occurrence.

In some implementations, operation 702 may include an operation 706 for correlating the subjective user state data with the objective occurrence data based, at least in part, on a determination of whether the at least one subjective user state occurred before, after, or at least partially concurrently with incidence of the at least one objective occurrence as depicted in FIG. 7*a*. For instance, the correlation module 106 of the computing device 10 correlating the subjective user state data 60 with the objective occurrence data 70* based, at least in part, on a determination by the temporal relationship determination module 239 of whether the at least one subjective user state occurred before, after, or at least partially concurrently with incidence of the at least one objective occurrence.

In some implementations, operation 702 may include an operation 708 for correlating the subjective user state data with the objective occurrence data based, at least in part, on referencing of historical data as depicted in FIG. 7*a*. For instance, the correlation module 106 of the computing device 10 correlating the subjective user state data 60 with the objective occurrence data 70* based, at least in part, on referencing by the historical data referencing module 241 of historical data 72 (e.g., population trends such as the superior efficacy of ibuprofen as opposed to acetaminophen in reducing toothaches in the general population, user medical data such as genetic, metabolome, or proteome information, historical sequential patterns particular to the user 20* or to the overall population such as people having a hangover after drinking excessively, and so forth).

In various implementations, operation 708 may include one or more additional operations. For example, in some implementations, operation 708 may include an operation 710 for correlating the subjective user state data with the objective occurrence data based, at least in part, on the historical data indicative of a link between a subjective user state type and an objective occurrence type as depicted in FIG. 7*a*. For instance, the correlation module 106 of the computing device 10 correlating the subjective user state data 60 with the objective occurrence data 70* based, at least in part, on the historical data referencing module 241 referencing historical data 72 indicative of a link between a subjective user state type and an objective occurrence type (e.g., historical data 72 suggests or indicate a link between a person's mental well-being and exercise).

In some instances, operation 710 may further include an operation 712 for correlating the subjective user state data with the objective occurrence data based, at least in part, on a historical sequential pattern as depicted in FIG. 7*a*. For instance, the correlation module 106 of the computing device 10 correlating the subjective user state data 60 with the objective occurrence data 70* based, at least in part, on a historical sequential pattern (e.g., a historical sequential pattern that indicates that people feel more alert after exercising).

In some implementations, operation 708 may include an operation 714 for correlating the subjective user state data with the objective occurrence data based, at least in part, on historical medical data associated with the user as depicted in FIG. 7a. For instance, the correlation module 106 of the computing device 10 correlating the subjective user state data 60 with the objective occurrence data 70* based, at least in part, on historical medical data associated with the user 20* (e.g., genetic, metabolome, or proteome information or medical records of the user 20* or of others related to, for example, diabetes or heart disease).

Figure 7B:
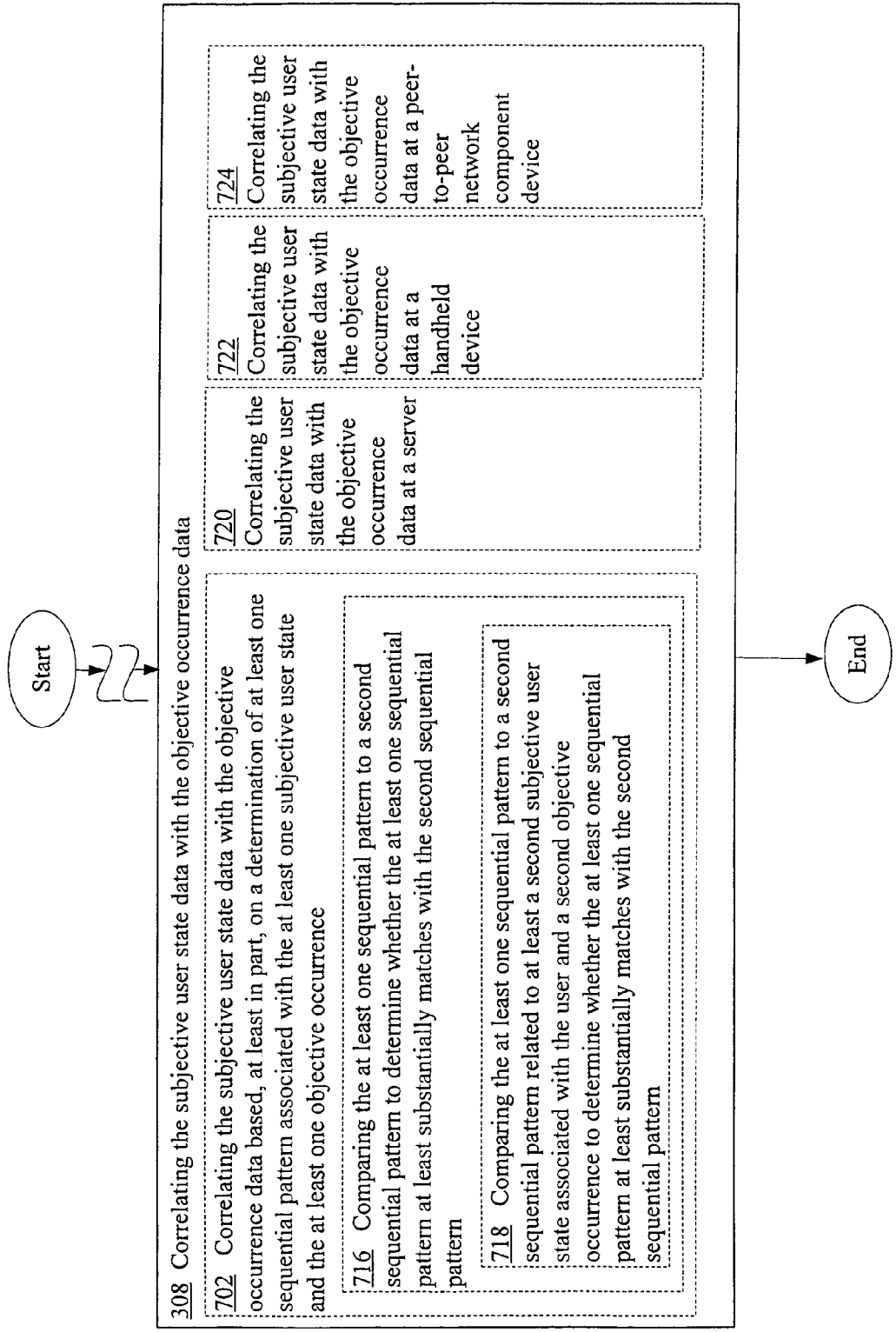
FIG. 7b is a high-level logic flowchart of a process depicting alternate implementations of the correlation operation 308 of FIG. 3.

In some implementations, operation 702 may include an operation 716 for comparing the at least one sequential pattern to a second sequential pattern to determine whether the at least one sequential pattern at least substantially matches with the second sequential pattern as depicted in FIG. 7b. For instance, the sequential pattern comparison module 242 of the computing device 10 comparing the at least one sequential pattern to a second sequential pattern to determine whether the at least one sequential pattern at least substantially matches with the second sequential pattern.

In various implementations, operation 716 may further include an operation 718 for comparing the at least one sequential pattern to a second sequential pattern related to at least a second subjective user state associated with the user and a second objective occurrence to determine whether the at least one sequential pattern at least substantially matches with the second sequential pattern as depicted in FIG. 7b. For instance, the sequential pattern comparison module 242 of the computing device 10 comparing the at least one sequential pattern to a second sequential pattern related to at least a second subjective user state associated with the user 20* and a second objective occurrence to determine whether the at least one sequential pattern at least substantially matches with the second sequential pattern. In other words, comparing the at least one subjective user state and the at least one objective occurrence associated with the one sequential pattern to the at least a second subjective user state and the at least a second objective occurrence associated with the second sequential pattern in order to determine whether they substantially match (or do not match) as well as to determine whether the temporal or time relationships associated with the one sequential pattern and the second sequential pattern substantially match.

In some implementations, the correlation operation 308 of FIG. 3 may include an operation 720 for correlating the subjective user state data with the objective occurrence data at a server as depicted in FIG. 7b. For instance, the correlation module 106 of the computing device 10 correlating the subjective user state data 60 with the objective occurrence data 70* when the computing device 10 is a network server.

In some implementations, the correlation operation 308 may include an operation 722 for correlating the subjective user state data with the objective occurrence data at a handheld device as depicted in FIG. 7b. For instance, the correlation module 106 of the computing device 10 correlating the subjective user state data 60 with the objective occurrence data 70* when the computing device 10 is a handheld device.

In some implementations, the correlation operation 308 may include an operation 724 for correlating the subjective user state data with the objective occurrence data at a peer-to-peer network component device as depicted in FIG. 7b. For instance, the correlation module 106 of the computing device 10 correlating the subjective user state data 60 with the objective occurrence data 70* when the computing device 10 is a peer-to-peer network component device.

Figure 8:
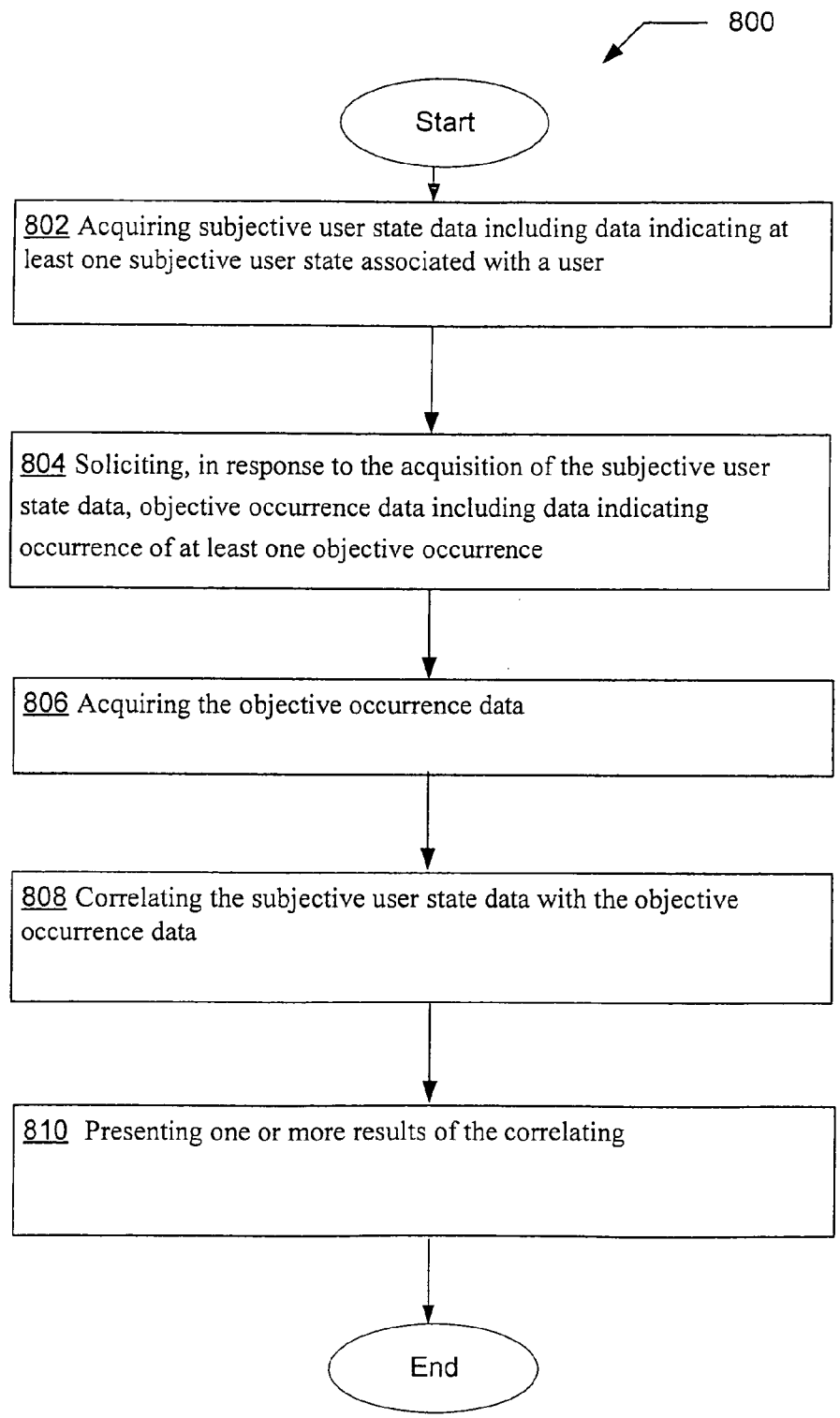
FIG. 8 is a high-level logic flowchart of another process.

Referring to FIG. 8 illustrating another operational flow 800 in accordance with various embodiments. Operational flow 800 includes operations that mirror the operations included in the operational flow 300 of FIG. 3. These operations include a subjective user state data acquisition operation 802, an objective occurrence data solicitation operation 804, an objective occurrence data acquisition operation 806, and a correlation operation 808 that correspond to and mirror the subjective user state data acquisition operation 302, the objective occurrence data solicitation operation 304, the objective occurrence data acquisition operation 306, and the correlation operation 308, respectively, of FIG. 3.

In addition, operational flow 800 includes a presentation operation 810 for presenting one or more results of the correlating as depicted in FIG. 8. For example, the presentation module 108 of the computing device 10 presenting (e.g., transmitting via a network interface 120 or providing via the user interface 122) one or more results of the correlating operation as performed by the correlation module 106.

Figure 9:
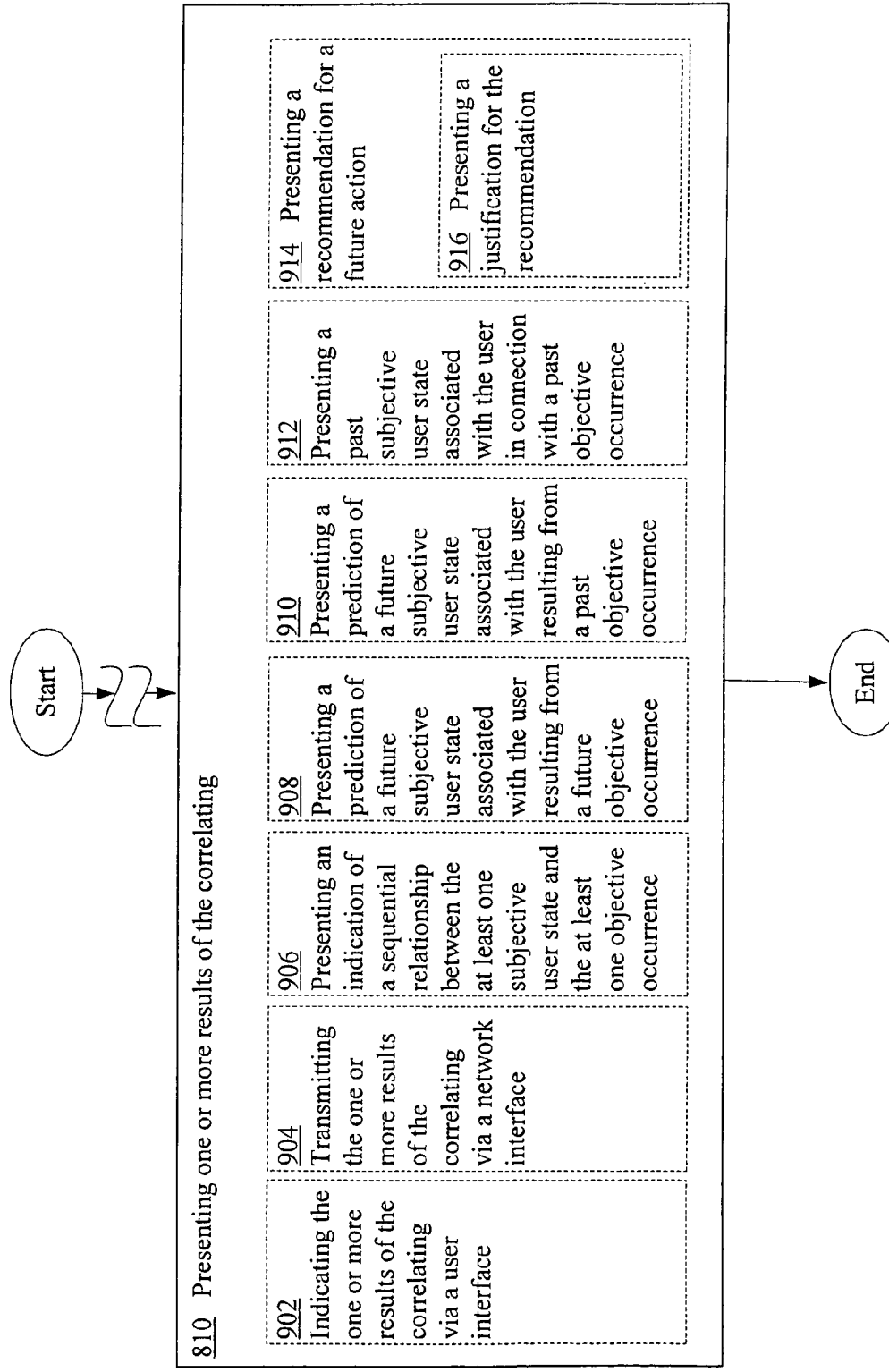
FIG. 9 is a high-level logic flowchart of a process depicting alternate implementations of the presentation operation 810 of FIG. 8.

In various embodiments, the presentation operation 810 may include one or more additional operations as depicted in FIG. 9. For example, in some implementations, the presentation operation 810 may include an operation 902 for indicating the one or more results of the correlating via a user interface. For instance, the user interface indication module 254 (see FIG. 2e) of the computing device 10 indicating (e.g., displaying or audibly indicating) the one or more results (e.g., in the form of an advisory, a warning, an alert, a prediction, and so forth of a future or past result) of the correlating operation performed by the correlation module 106 via a user interface 122 (e.g., display monitor, touchscreen, or audio system including one or more speakers).

In some implementations, the presentation operation 810 may include an operation 904 for transmitting the one or more results of the correlating via a network interface. For instance, the network interface transmission module 252 (see FIG. 2e) of the computing device 10 transmitting the one or more results (e.g., in the form of an advisory, a warning, an alert, a prediction, and so forth of a future or past result) of the correlating operation performed by the correlation module 106 via a network interface 120 (e.g., NIC).

In some implementations, the presentation operation 810 may include an operation 906 for presenting an indication of a sequential relationship between the at least one subjective user state and the at least one objective occurrence. For instance, the sequential relationship presentation module 256 of the computing device 10 presenting (e.g., transmitting via the network interface 120 or indicating via user interface 122) an indication of a sequential relationship between the at least one subjective user state (e.g., headache) and the at least one objective occurrence (e.g., drinking beer).

In some implementations, the presentation operation 810 may include an operation 908 for presenting a prediction of a future subjective user state associated with the user resulting from a future objective occurrence. For instance, the prediction presentation module 258 of the computing device 10 a prediction of a future subjective user state associated with the user 20* resulting from a future objective occurrence. An example prediction might state that "if the user drinks five shots of whiskey tonight, the user will have a hangover tomorrow."

In some implementations, the presentation operation 810 may include an operation 910 for presenting a prediction of a future subjective user state associated with the user resulting from a past objective occurrence. For instance, the prediction presentation module 258 of the computing device 10 presenting a prediction of a future subjective user state associated with the user 20* resulting from a past objective occurrence.

An example prediction might state that "the user will have a hangover tomorrow since the user drank five shots of whiskey tonight."

In some implementations, the presentation operation 810 may include an operation 912 for presenting a past subjective user state associated with the user in connection with a past objective occurrence. For instance, the past presentation module 260 of the computing device 10 presenting a past subjective user state associated with the user 20* in connection with a past objective occurrence. An example of such a presentation might state that "the user got depressed the last time it rained."

In some implementations, the presentation operation 810 may include an operation 914 for presenting a recommendation for a future action. For instance, the recommendation module 262 of the computing device 10 presenting a recommendation for a future action. An example recommendation might state that "the user should not drink five shots of whiskey."

Operation 914 may, in some instances, include an additional operation 916 for presenting a justification for the recommendation. For instance, the justification module 264 of the computing device 10 presenting a justification for the recommendation. An example justification might state that "the user should not drink five shots of whiskey because the last time the user drank five shots of whiskey, the user got a hangover."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system in the form of a machine, article of manufacture, or composition of matter, comprising:
    a subjective user state data acquisition module configured to acquire at least subjective user state data indicating at least one subjective user state associated with a user;
    an objective occurrence data solicitation module configured to solicit objective occurrence data in response to the acquisition of the subjective user state data;
    an objective occurrence data acquisition module configured to acquire the objective occurrence data including data indicating occurrence of at least one objective occurrence; and
    a correlation module configured to correlate the acquired subjective user state data with the acquired objective occurrence data.

2. The system of claim 1, where said subjective user state data acquisition module configured to acquire at least subjective user state data indicating at least one subjective user state associated with a user comprises:
    a subjective user state data reception module configured to receive at least the subjective user state data indicating at least one subjective user state associated with a user.

3. The system of claim 2, where said subjective user state data reception module configured to receive at least the subjective user state data indicating at least one subjective user state associated with a user comprises:
    a user interface data reception module configured to receive at least the subjective user state data indicating at least one subjective user state associated with a user.

4. The system of claim 2, where said subjective user state data reception module configured to receive at least the subjective user state data indicating at least one subjective user state associated with a user comprises:
    a network interface data reception module configured to receive at least the subjective user state data indicating at least one subjective user state associated with a user.

5. The system of claim 4, where said network interface data reception module configured to receive at least the subjective user state data indicating at least one subjective user state associated with a user comprises:

a network interface data reception module configured to receive, via an electronic message generated by the user, the subjective user state data.

6. The system of claim 4, where said network interface data reception module configured to receive at least the subjective user state data indicating at least one subjective user state associated with a user comprises:
a network interface data reception module configured to receive, via a blog entry generated by the user, the subjective user state data.

7. The system of claim 4, where said network interface data reception module configured to receive at least the subjective user state data indicating at least one subjective user state associated with a user comprises:
a network interface data reception module configured to receive, via a status report generated by the user, the subjective user state data.

8. The system of claim 2, where said subjective user state data reception module configured to receive at least the subjective user state data indicating at least one subjective user state associated with a user comprises:
a subjective user state data reception module configured to receive a selection made by the user, the selection being a selection of a subjective user state from a plurality of indicated alternative subjective user states.

9. The system of claim 1, where said subjective user state data acquisition module configured to acquire at least subjective user state data indicating at least one subjective user state associated with a user comprises:
a subjective user state data acquisition module configured to acquire subjective user state data that indicates at least one subjective mental state of the user.

10. The system of claim 1, where said subjective user state data acquisition module configured to acquire at least subjective user state data indicating at least one subjective user state associated with a user comprises:
a subjective user state data acquisition module configured to acquire subjective user state data that indicates at least one subjective physical state of the user.

11. The system of claim 1, where said subjective user state data acquisition module configured to acquire at least subjective user state data indicating at least one subjective user state associated with a user comprises:
a subjective user state data acquisition module configured to acquire subjective user state data that indicates at least one subjective overall state of the user.

12. The system of claim 1, where said subjective user state data acquisition module configured to acquire at least subjective user state data indicating at least one subjective user state associated with a user comprises:
a time stamp acquisition module configured to acquire a time stamp, the time stamp being associated with an occurrence of the at least one subjective user state associated with the user.

13. The system of claim 1, where said subjective user state data acquisition module configured to acquire at least subjective user state data indicating at least one subjective user state associated with a user comprises:
a time interval acquisition module configured to acquire a time interval, the time interval being associated with an occurrence of the at least one subjective user state associated with the user.

14. The system of claim 1, where said objective occurrence data solicitation module configured to solicit objective occurrence data in response to the acquisition of the subjective user state data comprises:
an objective occurrence data solicitation module configured to solicit the objective occurrence data from the user.

15. The system of claim 14, where said objective occurrence data solicitation module configured to solicit the objective occurrence data from the user comprises:
a user interface solicitation module configured to solicit, via a user interface, the objective occurrence data.

16. The system of claim 14, where said objective occurrence data solicitation module configured to solicit the objective occurrence data from the user comprises:
a network interface solicitation module configured to solicit, via a network interface, the objective occurrence data.

17. The system of claim 14, where said objective occurrence data solicitation module configured to solicit the objective occurrence data from the user comprises:
a requesting module configured to request a confirmation of an occurrence of at least one objective occurrence from the user.

18. The system of claim 14, where said objective occurrence data solicitation module configured to solicit the objective occurrence data from the user comprises:
a requesting module configured to request a selection by the user of at least one objective occurrence from a plurality of indicated alternative objective occurrences.

19. The system of claim 14, where said objective occurrence data solicitation module configured to solicit the objective occurrence data from the user comprises:
a requesting module configured to request from the user an indication of occurrence of at least one objective occurrence with respect to occurrence of the at least one subjective user state.

20. The system of claim 14, where said objective occurrence data solicitation module configured to solicit the objective occurrence data from the user comprises:
a requesting module configured to request from the user an indication of occurrence of at least one objective occurrence associated with a particular type of objective occurrence.

21. The system of claim 14, where said objective occurrence data solicitation module configured to solicit the objective occurrence data from the user comprises:
a requesting module configured to request from the user an indication of a time or temporal element associated with occurrence of at least one objective occurrence.

22. The system of claim 21, where said requesting module configured to request from the user an indication of a time or temporal element associated with occurrence of at least one objective occurrence comprises:
a requesting module configured to request from the user an indication of a point in time associated with the occurrence of at least one objective occurrence.

23. The system of claim 21, where said requesting module configured to request from the user an indication of a time or temporal element associated with occurrence of at least one objective occurrence comprises:
a requesting module configured to request from the user an indication of a time interval associated with the occurrence of at least one objective occurrence.

24. The system of claim 14, where said objective occurrence data solicitation module configured to solicit the objective occurrence data from the user comprises:
a requesting module configured to request from the user an indication of temporal relationship between occurrence of at least one objective occurrence and occurrence of one subjective user state.

25. The system of claim 1, where said objective occurrence data solicitation module configured to solicit objective occurrence data in response to the acquisition of the subjective user state data comprises:
- an objective occurrence data solicitation module configured to solicit objective occurrence data from one or more third party sources.

26. The system of claim 25, where said objective occurrence data solicitation module configured to solicit objective occurrence data from one or more third party sources comprises:
- a requesting module configured to request data from one or more other users that indicates occurrence of at least one objective occurrence.

27. The system of claim 25, where said objective occurrence data solicitation module configured to solicit objective occurrence data from one or more third party sources comprises:
- a requesting module configured to request data from one or more healthcare entities that indicates occurrence of at least one objective occurrence.

28. The system of claim 25, where said objective occurrence data solicitation module configured to solicit objective occurrence data from one or more third party sources comprises:
- a requesting module configured to request data from one or more content providers that indicates occurrence of at least one objective occurrence.

29. The system of claim 25, where said objective occurrence data solicitation module configured to solicit objective occurrence data from one or more third party sources comprises:
- a requesting module configured to request data from one or more other users that indicates occurrence of at least one objective occurrence that occurred at a specified point in time.

30. The system of claim 25, where said objective occurrence data solicitation module configured to solicit objective occurrence data from one or more third party sources comprises:
- a requesting module configured to request data from one or more other users that indicates occurrence of at least one objective occurrence that occurred during a specified time interval.

31. The system of claim 1, where said objective occurrence data solicitation module configured to solicit objective occurrence data in response to the acquisition of the subjective user state data comprises:
- an objective occurrence data solicitation module configured to solicit data from one or more sensors that indicates occurrence of at least one objective occurrence.

32. The system of claim 31, where said objective occurrence data solicitation module configured to solicit data from one or more sensors that indicates occurrence of at least one objective occurrence comprises:
- a configuration module designed to configure the one or more sensors to at least collect and provide data indicating occurrence of at least one objective occurrence.

33. The system of claim 31, where said objective occurrence data solicitation module configured to solicit data from one or more sensors that indicates occurrence of at least one objective occurrence comprises:
- a directing/instructing module configured to direct or instruct the one or more sensors to collect and provide data that indicates occurrence of at least one objective occurrence.

34. The system of claim 31, where said objective occurrence data solicitation module configured to solicit data from one or more sensors that indicates occurrence of at least one objective occurrence comprises:
- an objective occurrence data solicitation module configured to solicit objective occurrence data in response to the acquisition of the subjective user state data and based on historical data.

35. The system of claim 34, where said objective occurrence data solicitation module configured to solicit objective occurrence data in response to the acquisition of the subjective user state data and based on historical data comprises:
- an objective occurrence data solicitation module configured to solicit objective occurrence data based, at least in part, on one or more historical sequential patterns.

36. The system of claim 34, where said objective occurrence data solicitation module configured to solicit objective occurrence data in response to the acquisition of the subjective user state data and based on historical data comprises:
- an objective occurrence data solicitation module configured to solicit objective occurrence data based, at least in part, on medical data of the user.

37. The system of claim 34, where said objective occurrence data solicitation module configured to solicit objective occurrence data in response to the acquisition of the subjective user state data and based on historical data comprises:
- an objective occurrence data solicitation module configured to solicit objective occurrence data based, at least in part, on historical data indicative of a link between a subjective user state type and an objective occurrence type.

38. The system of claim 34, where said objective occurrence data solicitation module configured to solicit objective occurrence data in response to the acquisition of the subjective user state data and based on historical data comprises:
- an objective occurrence data solicitation module configured to solicit objective occurrence data, the solicitation of the objective occurrence data being prompted, at least in part, by the historical data.

39. The system of claim 34, where said objective occurrence data solicitation module configured to solicit objective occurrence data in response to the acquisition of the subjective user state data and based on historical data comprises:
- an objective occurrence data solicitation module configured to solicit objective occurrence data indicating occurrence of a particular type of objective occurrence based on the historical data.

40. The system of claim 1, where said objective occurrence data solicitation module configured to solicit objective occurrence data in response to the acquisition of the subjective user state data comprises:
- an objective occurrence data solicitation module configured to solicit objective occurrence data including data indicating one or more attributes associated with occurrence of at least one objective occurrence.

41. The system of claim 1, where said objective occurrence data solicitation module configured to solicit objective occurrence data in response to the acquisition of the subjective user state data comprises:
- an objective occurrence data solicitation module configured to solicit objective occurrence data by requesting access to the objective occurrence data.

42. A system, comprising:
- circuitry for acquiring at least subjective user state data indicating at least one subjective user state associated with a user;
- circuitry for soliciting objective occurrence data in response to the acquisition of the subjective user state data;
- circuitry for acquiring the objective occurrence data including data indicating occurrence of at least one objective occurrence; and
- circuitry for correlating the acquired subjective user state data with the acquired objective occurrence data.

43. An article of manufacture, comprising:

a non-transitory signal-bearing medium bearing:

one or more instructions for acquiring at least subjective user state data indicating at least one subjective user state associated with a user;

one or more instructions for soliciting objective occurrence data in response to the acquisition of the subjective user state data;

one or more instructions for acquiring the objective occurrence data including data indicating occurrence of at least one objective occurrence; and one or more instructions for correlating the acquired subjective user state data with the acquired objective occurrence data.

* * * * *